(12) United States Patent
Granger et al.

(10) Patent No.: US 6,197,540 B1
(45) Date of Patent: *Mar. 6, 2001

(54) PREPARATION AND STABILIZATION OF CELLS USING AGED TRANSITION METAL SOLUTIONS

(75) Inventors: Vivian Granger; David Barnett; John T. Reilly, all of Sheffield (GB); Petra S. M. Mayr, Oberschleissheim (DE); Shawn P. Fay, Princeton, NJ (US)

(73) Assignee: Northern General Hospital N.H.S. Trust

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/578,591

(22) PCT Filed: Jul. 5, 1994

(86) PCT No.: PCT/EP94/02189

§ 371 Date: Jun. 21, 1996

§ 102(e) Date: Jun. 21, 1996

(87) PCT Pub. No.: WO95/01796

PCT Pub. Date: Jan. 19, 1995

(30) Foreign Application Priority Data

| Jul. 5, 1993 | (GB) | 9313962 |
| Jul. 20, 1993 | (GB) | 9315871 |
| Apr. 5, 1994 | (GB) | 9406698 |

(51) Int. Cl.[7] ................................................. A61K 9/44
(52) U.S. Cl. ........................ 435/40.51; 435/40.5; 435/2
(58) Field of Search .......................... 436/10, 17; 435/2, 435/40.5, 40.51

(56) References Cited

U.S. PATENT DOCUMENTS

| 4,045,488 | 8/1977 | Sarges . | |
| 4,123,384 | 10/1978 | Hundt et al. . | |
| 4,152,208 | 5/1979 | Guirgis . | |
| 4,302,355 | * 11/1981 | Turner, Jr. et al. ................. | 252/408 |
| 4,324,687 | 4/1982 | Louderback et al. . | |
| 4,704,352 | 11/1987 | Miripol et al. . | |
| 4,806,343 | 2/1989 | Carpenter et al. . | |
| 4,833,090 | 5/1989 | Liss et al. . | |
| 5,270,208 | * 12/1993 | Ryan ...................................... | 436/10 |
| 5,407,794 | * 4/1995 | Kass ...................................... | 436/63 |
| 5,422,277 | * 6/1995 | Connelly et al. ...................... | 436/10 |
| 5,858,699 | * 1/1999 | Granger et al. ................... | 435/40.51 |

FOREIGN PATENT DOCUMENTS

| 1147004 | 4/1963 | (DE) . |
| 0030710 | 12/1980 | (EP) . |
| 0901675 | 7/1962 | (GB) . |
| 1302564 | 1/1973 | (GB) . |
| 1449228 | 9/1976 | (GB) . |
| 2001757 | 2/1979 | (GB) . |
| 1563839 | * 4/1980 | (GB) . |
| 1583320 | 1/1981 | (GB) . |
| 2077916 | 12/1981 | (GB) . |
| 2099281 | 12/1982 | (GB) . |
| 2279653 | 1/1995 | (GB) . |
| 5164758 | 6/1993 | (JP) . |
| 1767436 | 5/1990 | (SU) . |
| 8703484 | 6/1987 | (WO) . |
| 8705113 | 8/1987 | (WO) . |
| 9117436 | 11/1991 | (WO) . |
| 9219951 | 11/1992 | (WO) . |
| 9321928 | 11/1993 | (WO) . |
| 9407532 | 4/1994 | (WO) . |
| 9501796 | 1/1995 | (WO) . |
| 9527203 | 10/1995 | (WO) . |

OTHER PUBLICATIONS

Cornelis, R. et al., "Chromium Speciation Studies in Human Plasma and Stability Studies of Cr (III) and CR (VI) Species in a Candidate Water Reference Material"; *Mikrochim.Acta* 109: 145–148 (1992).

* cited by examiner

*Primary Examiner*—Sandra E. Saucier
(74) *Attorney, Agent, or Firm*—Sheldon & Mak

(57) ABSTRACT

The invention is directed to novel stabilized blood compositions and methods of stabilizing blood compositions for use in the quality control of analytical techniques. The novel blood compositions comprise leucocytes and an effective amount of an aged transition metal solution. The novel method comprises removing leucocytes from a blood composition to yield a depleted blood composition, stabilizing the leucocytes by treatment with an effective amount of a stabilizing agent comprising an aged transition metal solution, and then, adding the resultant stabilized leucocytes to the depleted blood composition or a second blood component composition.

36 Claims, 20 Drawing Sheets

FSC
GATED EVENTS: 3646
TOTAL EVENTS: 15000

FSC
GATED EVENTS: 2409
TOTAL EVENTS: 15000

FSC
GATED EVENTS: 3149
TOTAL EVENTS: 15000

FSC
GATED EVENTS: 7289
TOTAL EVENTS: 50000

FIG.3a(ii)
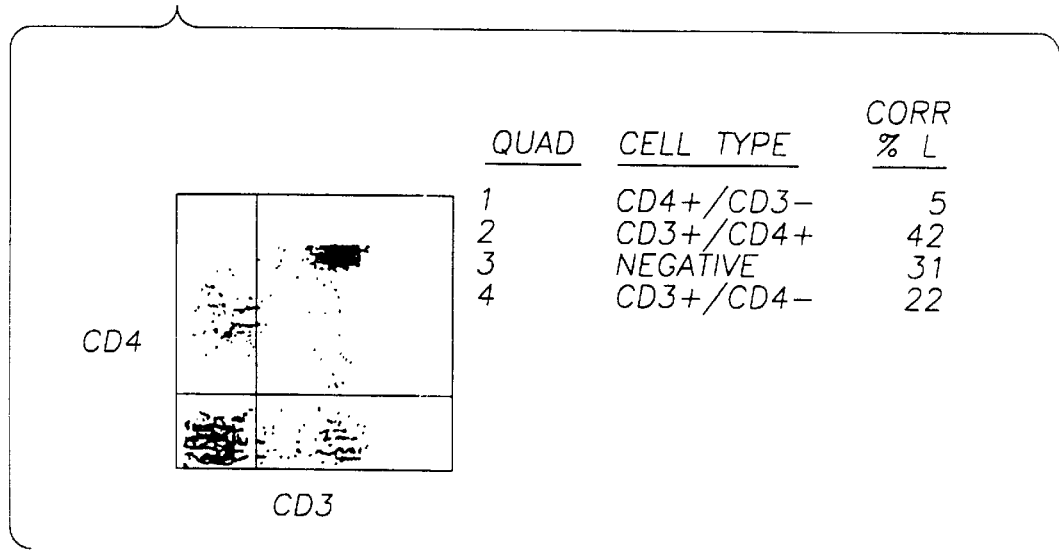
FIG.3b(ii)
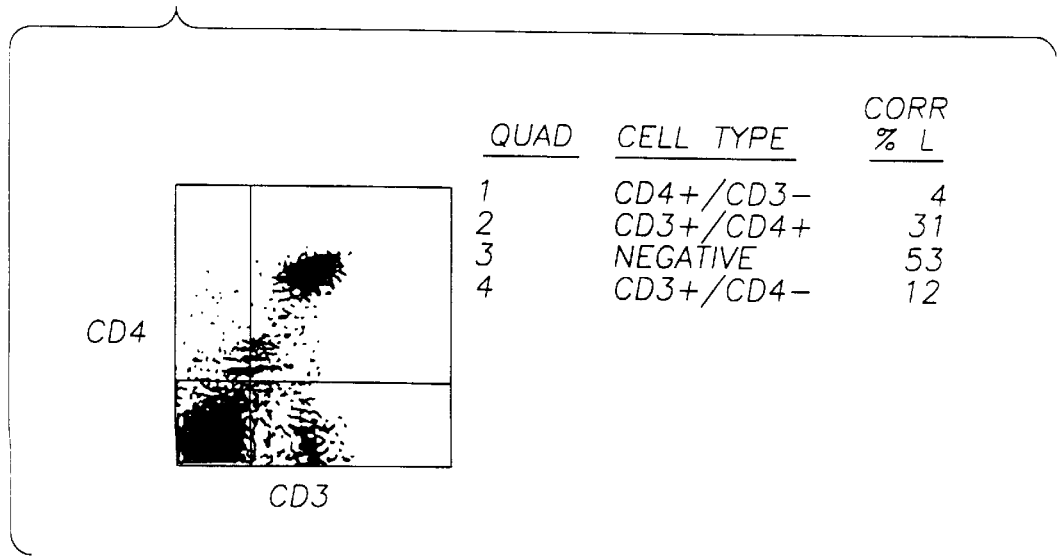

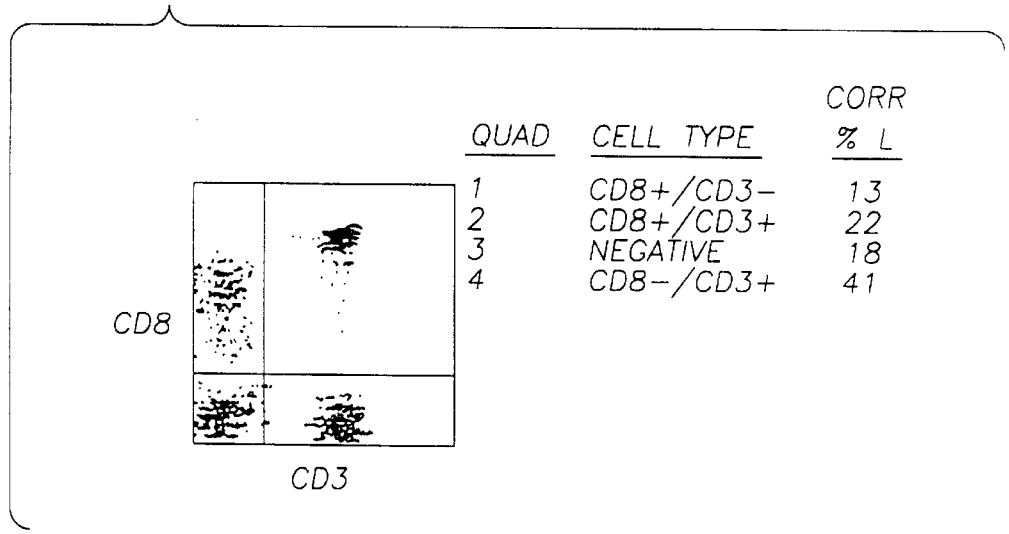
FIG.3a(iii)
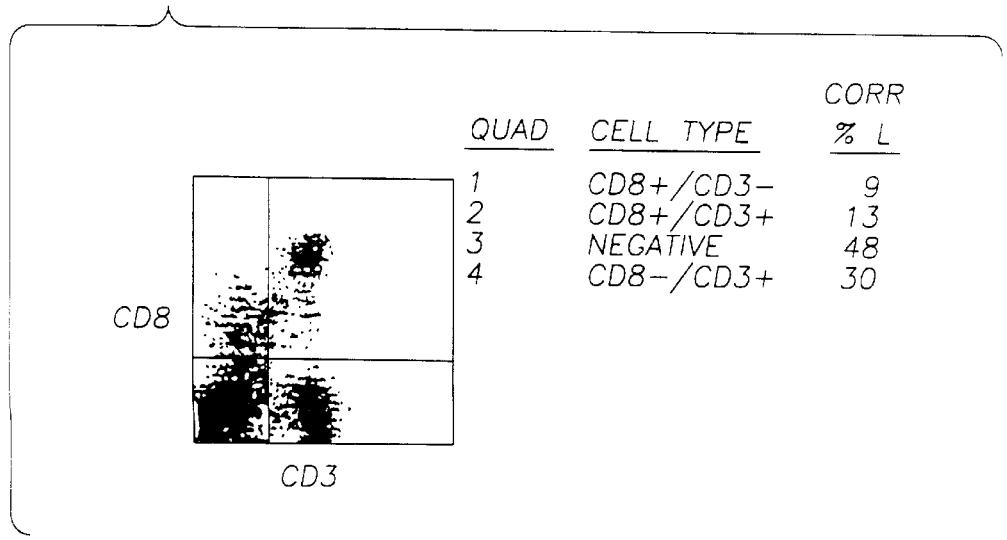
FIG.3b(iii)

FIG.4a(i)
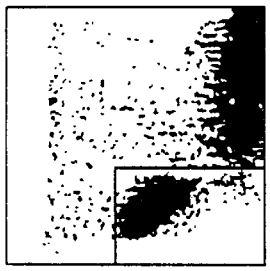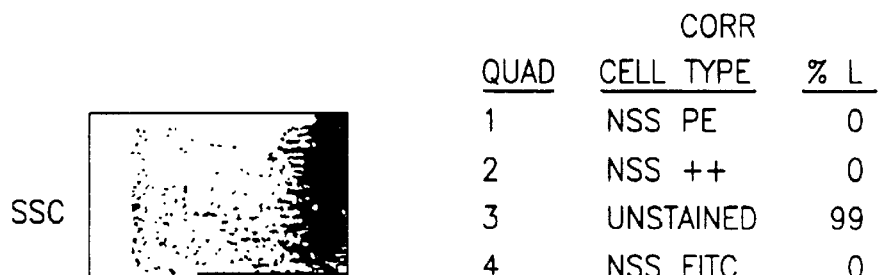
GATED EVENTS: 3987
TOTAL EVENTS: 15000
| QUAD | CELL TYPE | CORR % L |
|---|---|---|
| 1 | NSS PE | 0 |
| 2 | NSS ++ | 0 |
| 3 | UNSTAINED | 99 |
| 4 | NSS FITC | 0 |
FIG.4a(ii)
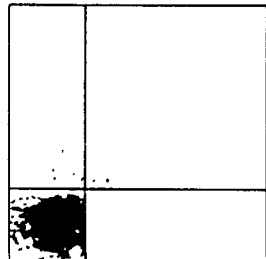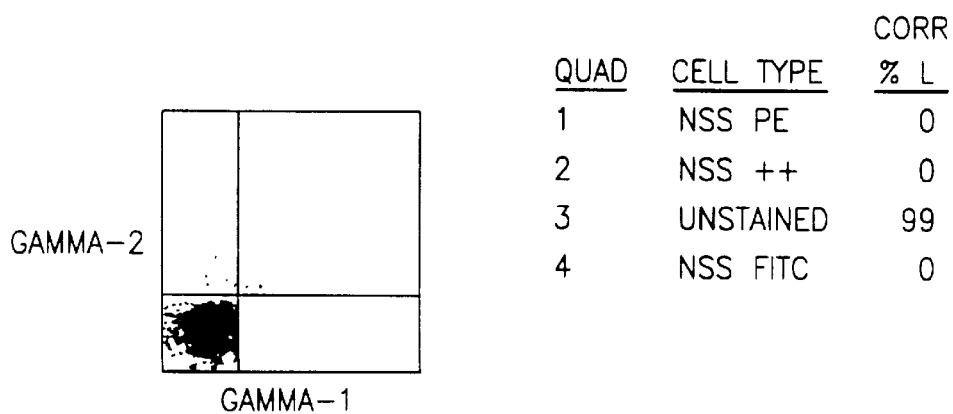
| QUAD | CELL TYPE | CORR % L |
|---|---|---|
| 1 | NSS PE | 0 |
| 2 | NSS ++ | 0 |
| 3 | UNSTAINED | 99 |
| 4 | NSS FITC | 0 |

FIG.4b(i)
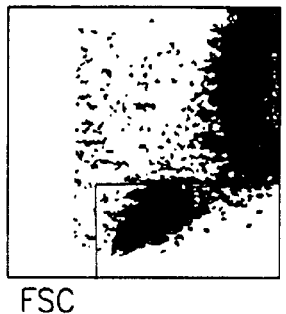
| QUAD | CELL TYPE | CORR % L |
|---|---|---|
| 1 | NSS PE | 0 |
| 2 | NSS ++ | 0 |
| 3 | UNSTAINED | 100 |
| 4 | NSS FITC | 0 |
GATED EVENTS: 4824
TOTAL EVENTS: 15000
FIG.4b(ii)
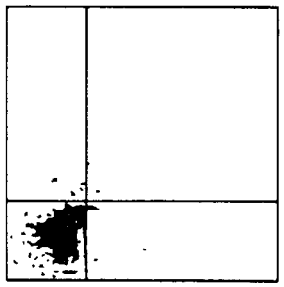
| QUAD | CELL TYPE | CORR % L |
|---|---|---|
| 1 | NSS PE | 0 |
| 2 | NSS ++ | 0 |
| 3 | UNSTAINED | 100 |
| 4 | NSS FITC | 0 |

FIG.5a(i)
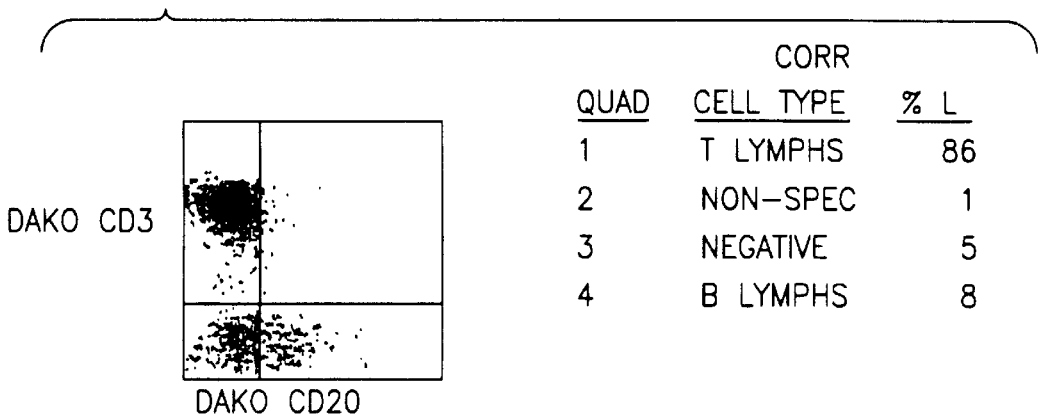
| QUAD | CELL TYPE | CORR % L |
|---|---|---|
| 1 | T LYMPHS | 86 |
| 2 | NON-SPEC | 1 |
| 3 | NEGATIVE | 5 |
| 4 | B LYMPHS | 8 |
FIG.5b(i)
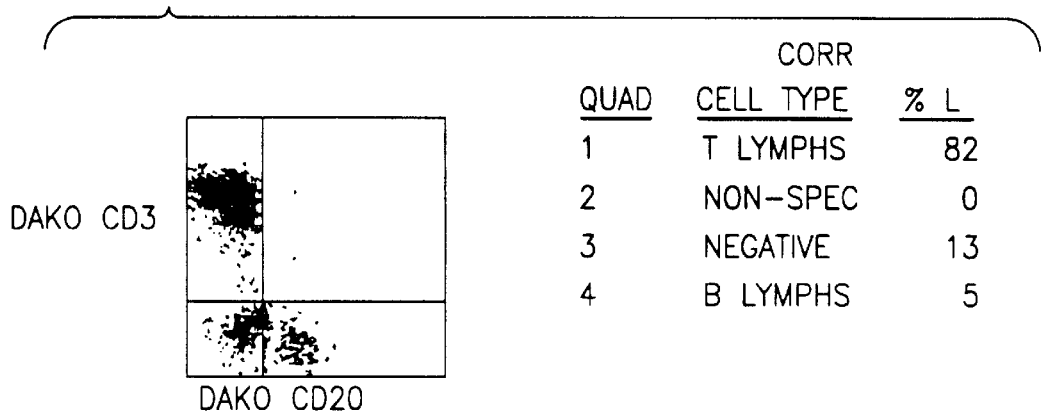
| QUAD | CELL TYPE | CORR % L |
|---|---|---|
| 1 | T LYMPHS | 82 |
| 2 | NON-SPEC | 0 |
| 3 | NEGATIVE | 13 |
| 4 | B LYMPHS | 5 |
FIG.5a(ii)
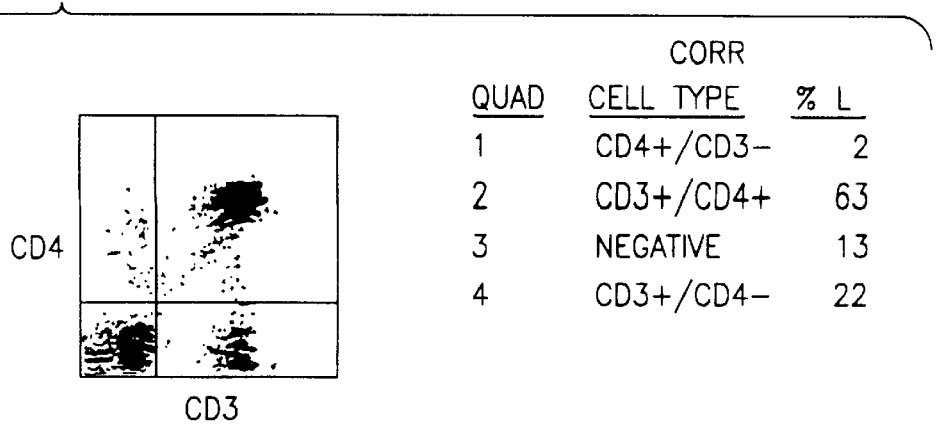
| QUAD | CELL TYPE | CORR % L |
|---|---|---|
| 1 | CD4+/CD3- | 2 |
| 2 | CD3+/CD4+ | 63 |
| 3 | NEGATIVE | 13 |
| 4 | CD3+/CD4- | 22 |

FIG.5b(ii)
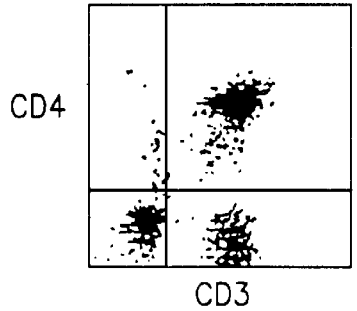
| QUAD | CORR CELL TYPE | % L |
|---|---|---|
| 1 | CD4+/CD3− | 2 |
| 2 | CD3+/CD4+ | 62 |
| 3 | NEGATIVE | 15 |
| 4 | CD3+/CD4− | 22 |
FIG.5a(iii)
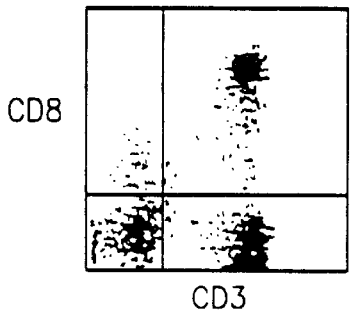
| QUAD | CORR CELL TYPE | % L |
|---|---|---|
| 1 | CD8+/CD3− | 2 |
| 2 | CD8+/CD3+ | 22 |
| 3 | NEGATIVE | 13 |
| 4 | CD8−/CD3+ | 63 |
FIG.5b(iii)
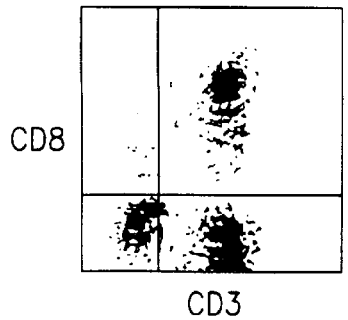
| QUAD | CORR CELL TYPE | % L |
|---|---|---|
| 1 | CD8+/CD3− | 0 |
| 2 | CD8+/CD3+ | 21 |
| 3 | NEGATIVE | 16 |
| 4 | CD8−/CD3+ | 63 |

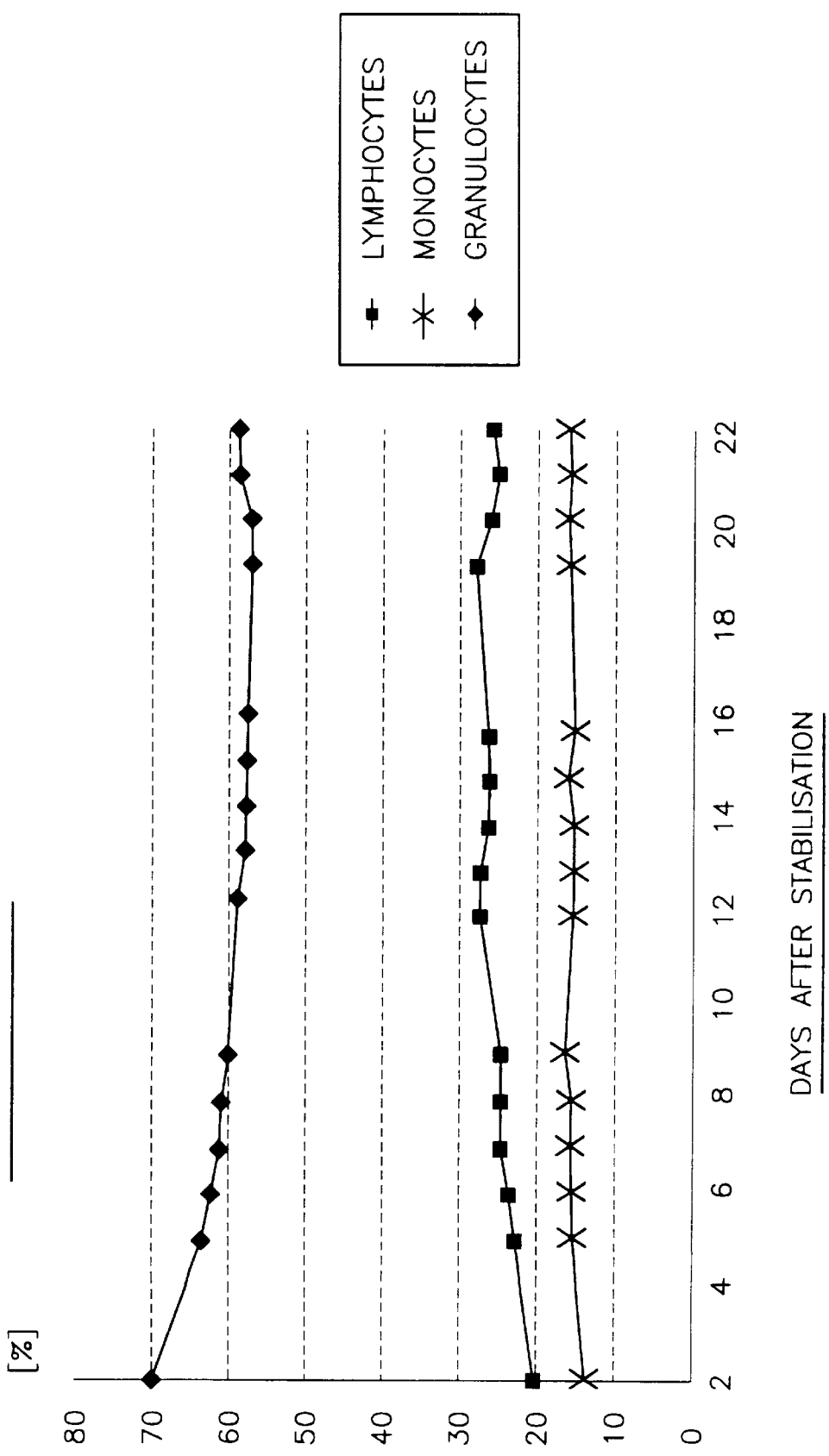

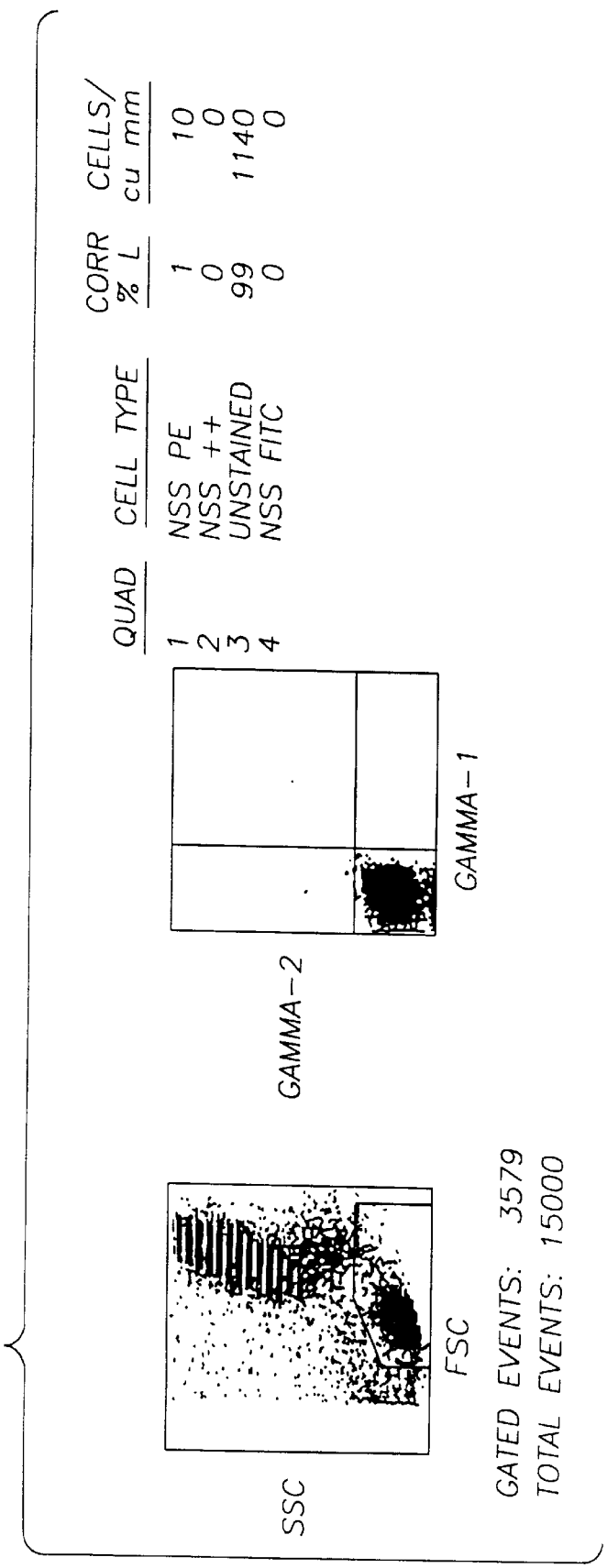

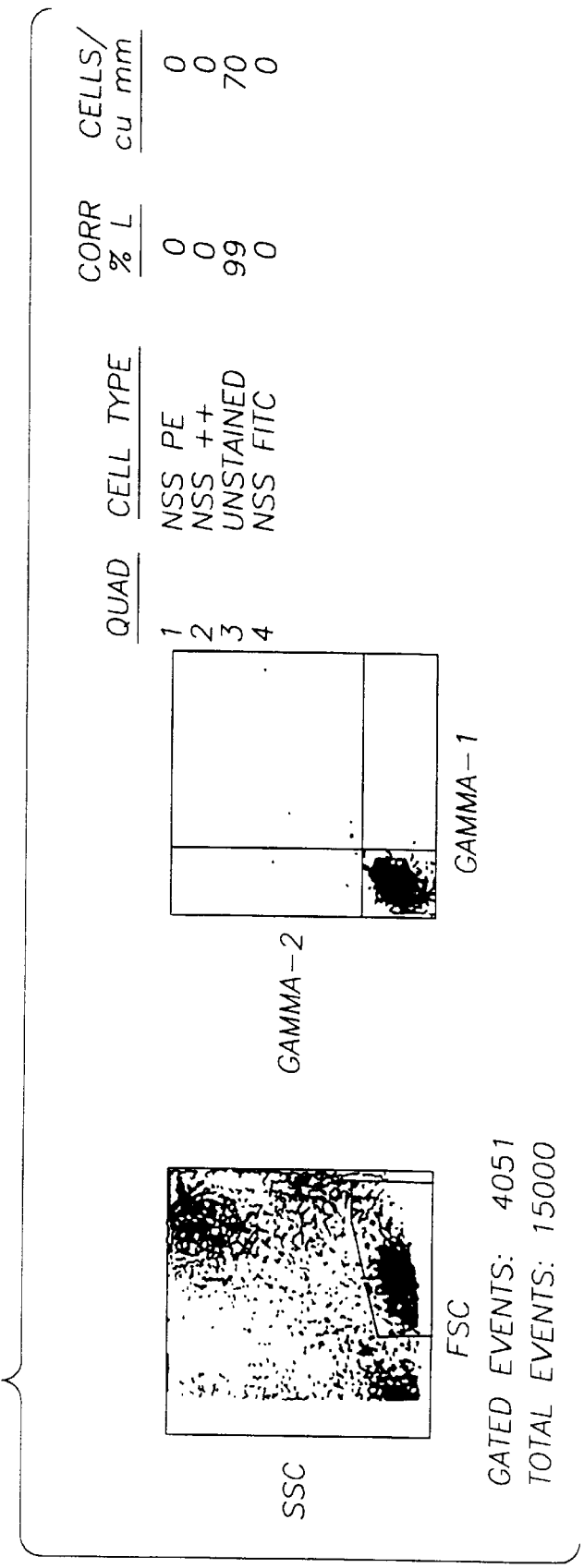

PREPARATION AND STABILIZATION OF CELLS USING AGED TRANSITION METAL SOLUTIONS

BACKGROUND OF THE INVENTION

This invention relates to the preparation and stabilisation of cells, and more particularly to a novel method for preparing and stabilising cells and cell suspensions, especially whole blood and constituents thereof and to the use of novel stabilised cell preparations in the quality control of analytical techniques such as UV microscopy and flow cytometric leucocyte immunophenotyping techniques, immobilised antigen/antibody detection systems and haematology analysers, and blood monitoring techniques such as zinc protoporphyrin (ZPP), red cell folate and blood glucose measurements.

UV microscopy and flow cytometry are techniques used in the diagnosis of haematological malignancies. They are also used to monitor the progress of patients infected with the Human Immunodeficiency Virus (HIV), whether asymptomatic or suffering from ARC or full-blown AIDS. Quality control (QC) of these two techniques is extremely important to arrive at the correct diagnosis and to monitor effective therapeutic regimes. The current QC methods use freshly drawn blood or microspheres coated with a fluorochrome.

The use of fresh blood on a daily basis fails to provide the information on day-to-day variation of the technique or equipment. Furthermore, fluorochrome coated microspheres, though providing a day-to-day monitor of the flow cytometer's performance, cannot be used for UV microscopy work. In addition, they cannot be used to provide quality control for the labelling techniques of leucocytes.

Fixation of normal leucocytes utilising compounds such as aldehydes, although giving stability for 5–7 days, increases cellular autofluorescence. This makes the preparation unsuitable for use as a long-term quality control material. Furthermore, the lysis of red cells by the whole blood lysing technique requires a preparation that will quality control this procedure. The current methods of fixing the leucocytes inhibit this lysing procedure, resulting in a significant increase in debris that interferes with the tests.

In International Application No. PCT/US91/03236, the entire disclosure of which is incorporated herein by reference, there is described a blood diluent and lysing agent for differential determination of white blood cells (leucocytes) in which the stabilising agent is diazolidinyl urea. Such leucocyte preparations have not been suggested as quality control preparations, possibly because they have insufficient stability and lack certain specific antigenic activity for those routine quality control procedures which need to assess results from a large number of laboratories.

International Application No. PCT/US92/03758, the entire disclosure of which is incorporated herein by reference, discloses the use of diazolidinyl urea, imidazolidinyl urea, dimethylol-5, 5-dimethylhydantion, dimethylol urea, 2-bromo-2-nitropropane-1, 3-diol and quaternary adamantane as tissue fixatives which are free of aldehydes. The formulations may inter alia mordants such as zinc, strontium, calcium, barium and chromium salts. It is not suggested, however, that any of these salts have stabilising properties.

Other QC equipment requiring the use of whole blood samples or blood products for calibration include haematology analysers, where currently fixed bovine blood or blood from donkeys and turkeys is used because a suitable source of stabilised human blood is not available. Zinc protoporphyrin (ZPP) and red cell folate monitoring techniques also require a fresh suspension of red blood cells for calibration, again because a suitable stabilised source is not available. Finally the lack of a stabilised source of whole human blood for calibration purposes limits the possibility for diabetics to carry out blood sugar monitoring at home.

It will be appreciated from the above that there is a need for an improved method for stabilising cells, particularly of whole blood and blood products, for a variety of quality control, monitoring and calibration applications.

OBJECTS OF THE INVENTION

It is an object of the invention to provide an improved stabilised cell preparation and an improved method for stabilising cells.

It is also an object of the invention to provide a stabilised whole blood preparation and a method of manufacturing such a preparation.

It is a further object of the invention to provide an improved lysing procedure for the separation of leucocytes from red blood cells in whole blood.

It is a still further object of the invention to provide stable quality control materials which can be used in a wide spectrum of quality control, analysis and monitoring techniques.

SUMMARY OF THE INVENTION

It has now been discovered that a wide range of cells can be stabilised by the addition of a compound comprising a heavy metal to the cells in an effective amount, and that such stabilised cells will remain active for much longer periods than those known hitherto.

Thus in one aspect the invention provides a stabilised cell preparation in which the stabilising agent comprises an effective amount of a heavy metal compound.

In another aspect the invention provides a method of stabilising cells by adding thereto an effective amount of a stabilising agent comprising a heavy metal compound.

The invention is particularly applicable to the stabilisation of whole blood and of blood products and will be henceforth more particularly described with reference thereto. It is to be understood, however, that the invention is not limited to the stabilisation of such materials and is broadly applicable to a wide range of cellular materials and particularly cell suspensions.

In a further aspect, therefore, the invention provides a stabilised whole blood preparation in which the stabilising agent comprises an effective amount of a heavy metal compound and a method of stabilising a whole blood preparation by adding an effective amount of the compound thereto.

The invention also provides a method of stabilising the cellular constituents of whole blood, in particular leucocyte preparations formed for example from lysed whole blood, by the addition thereto of an effective amount of a heavy metal compound.

Thus, in a still further aspect, the invention provides a stabilised leucocyte preparation in which the stabilising agent comprises an effective amount of a heavy metal compound, and a method of stabilising a leucocyte preparation by the addition thereto of an effective amount of a stabilising agent comprising a heavy metal compound.

The stabilised leucocyte preparation of this aspect of the invention can be added to leucocyte depleted whole blood (red blood cells) to form a stabilised whole blood preparation, and the invention accordingly includes in a yet further aspect a stabilised whole blood preparation comprising leucocytes stabilised by the addition thereto of an effective amount of a stabilising agent, and a method of manufacturing a stabilised whole blood preparation which comprises adding a stabilised leucocyte preparation to leucocyte depleted whole blood.

In another aspect the invention provides a stabilised whole blood preparation which comprises stabilised leucocytes and untreated red blood cells.

In still another aspect the invention provides a novel stabilising agent for cellular materials, especially blood and blood products, which comprises an aqueous solution of a heavy metal compound and a formaldehyde.

In yet another aspect of the invention there is provided a lysing agent for the differentiation of leucocytes which comprises a solution of an ammonium or quaternary ammonium salt and a urea, the concentration of urea and the pH of the solution being sufficient to inhibit the monocytes from down-regulating the CD14 antigen sufficiently to allow their detection by immunological means.

BRIEF DESCRIPTION OF THE DRAWINGS

FIGS. 4a(I), 4a(ii), 4b(I), and 4b(ii) show the stability of FSC, SSC and the negative control characteristics, as determined by flow cytometry, upon the stabilised whole blood preparation, over a 57 day period;

FIGS. 5a(I), 5b(I), 5a(ii), 5b(ii), 5a(iii), 5b(iii) show the stability of the antigens shown in FIGS. 1b, 1c, and 1d, as measured by flow cytometry, over a 57 day period;

FIG. 7 shows the stability of the flow cytometric differential of the stabilised blood preparation over a 22 day period;

FIGS. 8a and 8b show the stability of FSC, SSC, and the negative control characteristics, as determined by flow cytometry, over a 60 day period;

DETAILED DESCRIPTION OF THE INVENTION

Figure 1A:
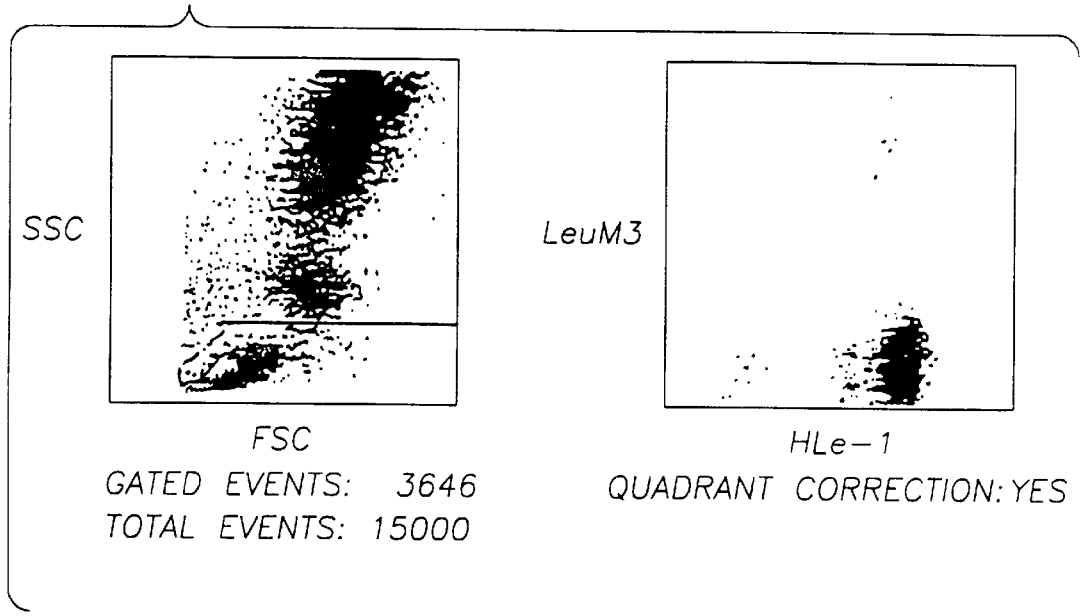
FIGS. 1a, 1b, 1c, and 1d show the flow cytometric characteristics of "fresh" blood after staining the antigens CD3, CD4, CD8, and CD20.

The invention will now be particularly described with reference to the manufacture of stabilised whole blood preparations for use in laboratory quality control procedures, although it will be appreciated that the invention is not limited thereto and that, for example, the stabilised whole blood preparations may find other uses, the stabilised leucocyte preparations may also find application as quality control materials, and that the stabilisation procedures described may find application in the manufacture of stabilised leucocytes from sources other than blood, for example intrathyroidal lymphocytes. In addition, the stabilisation procedures described may find application in the manufacture of stabilised cells from sources other than blood, for example microbial cells, plant cells and similar materials derived from living tissue.

Whole blood preparations in this specification include preparations containing substantially all the components of fresh blood, and preparations containing substantially all the components of fresh blood other than plasma.

The process by which the stabilisation of the whole blood is achieved uses a series of stages incorporating the addition of both organic and inorganic compounds. The initial process of drawing a unit of blood is well documented and can be any of those used by those employed in the art of venesection. Anticoagulated blood is preferably used, and several suitable anticoagulants are commercially available. However, the use of a potassium EDTA salt is preferred.

In accordance with a first procedure of the present invention, a stabilised whole blood preparation can be made by first separating the leucocytes from the red cells, stabilising the leucocytes, and then adding the stabilised leucocytes to leucocyte-depleted whole blood. In a second procedure, the leucocyte separation stage is omitted, and the stabilising agent is added to whole blood from which only the plasma has been removed. These two procedures will be separately described.

PROCEDURE I

The process of stabilising the leucocytes is usually performed within 24 hours of venesection but is preferably performed within 2 hours. To separate the leucocytes from the red cells, a novel process of red cell lysis is used.

The fresh whole blood, containing an anticoagulant, is first centrifuged, and the lysis performed on the buffy coat obtained after centrifuging. The lysing agent comprises a solution, preferably an aqueous solution, of an ammonium salt, for example ammonium chloride, or a quaternary ammonium salt and urea, or a suitable substituted urea or urea derivative. The concentration of the quaternary ammonium salt is preferable in the range of from 0.05 to 0.5M, and the concentration of the urea is less than 1.0M, and most preferably in the range of from 0.05 to 0.5M. The pH of the solution is preferably from 6.8 to 7.8. The lysis period is preferably from 5 to 20 minutes after which the resulting leucocytes are washed in isotonic saline solution to remove the lysed cell debris.

The leucocytes are then treated with a first stabilising agent which comprises a heavy metal compound, and particularly a heavy metal salt. Suitable heavy metals are those with complexing properties and having an atomic weight greater than 20, for example, transition metals, particularly transition metals of Groups IVa to VIIa of the Periodic Table, for example, manganese, chromium, molybdenum, vanadium and titanium, Group Ib, for example, copper, and Group IVb, for example tin. Group VIa and Group VIIa transition metals, and especially chromium and manganese, are particularly preferred. Suitable compounds include water-soluble salts of such metals, especially inorganic acid salts, for example sulphates and particularly chlorides. Particularly good results have been obtained using chromium compounds, for example chromium salts such as chromic chloride $CrCl_3$ and these are the preferred first stabilising agents for use in the present invention.

The heavy metal compound is preferably used in the form of a solution in a suitable solvent. This solvent will usually be water, or an aqueous medium, but additions of small quantities of less than 10% of suitable organic solvents which will not substantially inhibit the antigenic activity of the leucocytes or effect their integrity are not specifically excluded.

The presence of large amounts of organic solvents is, however, usually deleterious.

The solvent is preferably an isotonic aqueous solution buffered to a pH of from 6.5 to 7.0. Suitable buffered aqueous solutions include, for example, phosphate buffered saline solutions.

The heavy metal compound is preferably dissolved in the solvent and the solution allowed to stand, for example, for at least 6 hours, preferably 12 hours, more preferably 24 hours and most preferably 48 hours, for example one week before use. The reason why the performance of the solution improves with standing is not understood, but may be due to the formation of hydrated metal hydroxy ionic species in the solution. It has been observed with some buffered solutions of chromium compounds, for example, that the freshly made solutions change from green to purple over a 24 hour period, indicating the presence of charged complex ions, together with the formation of a precipitate which may be a chromium hydroxy polymeric species. This is preferably filtered off from the solution before use. The formation of a precipitate will of course lower the concentration of heavy metal ions in the solution, and of course if this should occur, an analysis of the solution should be carried out to determine whether the concentration of the first stabilising agent is still within the preferred range.

Preferably the heavy metal compound solution is stored as a relatively concentrated solution, for example, as a 1% w/v solution and is diluted with an appropriate buffer before use. On dilution a precipitate may form as the pH rises and sufficient time should be allowed for this to occur before the solution is used.

The aged solution of heavy metal compound retains its effectiveness over considerably periods of time, but is preferably discarded after 12 months and most preferably after 6 months.

The presence of the first stabilising agent can prevent the leucocytes from exhibiting excessive autofluorescence and at the same time can stabilise the leucocytes for a period of longer than 25 days. The first stabilising agent is preferably added to the leucocyte preparation as an isotonic solution in which the optimum final concentration of the first stabilising agent is preferably less than 1% w/v, more preferably from 0.005% to 0.75% w/v, still more preferably from 0.01% to 0.5% w/v and most preferably from 0.05 to 0.25% w/v, for example, 0.1% w/v. The solution is preferably a 0.85% phosphate buffered saline solution. The pH is preferably adjusted to from 6.5 to 7.0. The leucocytes are preferably exposed to the first stabilising agent for an incubation period of from 5 minutes to 18 hours but most preferably about 60 minutes. The incubation temperature is preferably from 0° C. to 8° C., for example about 4° C.

After the first incubation period, the leucocytes are preferably treated with a second stabilising agent which can be, for example, an aldehyde, preferably a formaldehyde, most preferably paraformaldehyde, which can, for example, be dissolved in a solution at a preferred final concentration of from 0.1% to 0.5% w/v, for example, 0.35% w/v.

Any suitable aldehyde may be used where cellular autofluorescence is not a problem, for example in certain histological techniques, but in general, and particularly when preparing samples for flow cytometry, autofluorescence needs to be kept to a minimum. In these circumstances paraformaldehyde is preferred since it give rise to least autofluorescence in most cases. When making up the paraformaldehyde solution it is preferable to keep the temperature below 60° C., in order to avoid the reversion of paraformaldehyde to formaldehyde.

It has been found that very good results are obtained using as the second stabilising agent an aqueous solution of a heavy metal compound and an aldehyde. This combined second stabilising agent is independently useful in the stabilisation of cellular materials and is accordingly a separate aspect of the invention.

The heavy metal compound may be any of those previously described, and may be present in the solution in an amount of from 0.01% to 0.5% w/v. The aldehyde can be present in an amount of from 0.1% to 0.5% w/v, and preferably the ratio of heavy metal compound to aldehyde in the solution is in the range of from 5:1 to 1:50. Preferably the solution has a pH of from 6.5 to 7.0, and may comprise a suitable isotonic buffer. A preferred solution can be, for example, a 0.85% phosphate buffered saline solution. Preferably the solution also comprises an anticoagulant, and preferred anticoagulants are EDTA and heparin. Exposure to the second stabilising solution is preferably from 6 hours to 24 hours at the temperature range designated above.

Although the heavy metal compounds, when used alone, have been found to have a significant stabilising effect for over 20 days in some cases, they have in general not been found to give stability for 60 days, which is regarded as a commercially desirable storage life.

A further improvement is obtained using a combined solution of a heavy metal compound and an aldehyde together (in effect, the second stabilising agent as previously described, used alone), but this treatment also has been found not to give the required 60 day stability in all cases.

On the other hand, the use of the first and second stabilising agents sequentially, as hitherto described, can give a leucocyte stability in excess of 220 days. The interval between the treatments with the first and second stabilising agents is preferably at least 30 minutes, more preferably at least one hour, most preferably at least 12 hours, for example 24 hours.

After washing in isotonic phosphate buffered saline solution, the stabilised leucocytes are added back to leucocyte depleted whole blood. This leucocyte depleted whole blood can but need not necessarily be obtained from the original donation by filtering the blood through a commercially available leucocyte filter. Bacterial growth inhibitors are preferably also added to the final preparation. The preparation is then retained at between 0° C. and 8° C. for 1 to 5 days before use.

All the above steps are preferably carried out under sterile conditions.

For the purposes of the present invention, the leucocyte depleted blood, comprising predominantly red blood cells, can be considered as being "untreated", in that it has been found that it is not necessary to add a stabilising agent to the leucocyte depleted blood in order to obtain a stabilised whole blood preparation. It is exceedingly surprising that it is possible to obtain a stabilised whole blood preparation by merely stabilising the leucocyte component thereof.

In the commercial manufacture of a stabilised whole blood preparation according to Procedure I, it is possible to pool a number of units of donated blood from different sources and to separate out and stabilise the leucocytes. Further units of blood from different donations can then be pooled and leucocyte depleted. Finally the pooled stabilised leucocyte preparation is added to the leucocyte depleted blood to form a stabilised whole blood preparation.

PROCEDURE II

This procedure is similar to that described in Procedure I except that, as previously mentioned, the leucocyte separation stage is omitted. For this reason, Procedure II will often be preferred for large-scale manufacture of stabilised whole blood preparations.

The process of stabilising the whole blood sample is usually performed within 24 hours of venesection but is preferably performed within 2 hours.

The fresh whole blood, containing an anticoagulant, for example EDTA, is first centrifuged, and the plasma removed and retained.

The remaining cells are washed and then treated with a first stabilising agent which comprises a heavy metal compound, which can be the same as that described in Procedure I.

The first stabilising agent is preferably added to the whole blood preparation as a solution in which the optimum final concentration of the first stabilising agent is preferably from 0.01% to 0.5% w/v. The solution is preferably in a 0.85% phosphate buffered saline solution. The pH is preferably adjusted to from 6.5 to 7.0. The whole blood is preferably exposed to the first stabilising agent for a period of from 5 minutes to 18 hours but most preferably about 60 minutes. The incubation temperature is preferably from 0° C. to 8° C., for example about 4° C.

After the first incubation period, the whole blood is preferably treated with a second stabilising agent which can be, for example, an aldehyde, preferably paraformaldehyde, using the same conditions as described for Procedure I. The addition of this second stabilising agent solution can extend the stability of the whole blood to in excess of 130 days. Exposure to the second stabilising solution is preferably from 6 hours to 24 hours, for example about 18 hours at the temperature range designated in Procedure I.

After washing in isotonic phosphate buffered saline solution, the plasma is added back to the stabilised whole blood. This plasma can, but need not necessarily be, that obtained from the original donation. Bacterial growth inhibitors and antibiotics, for example gentamycin, are preferably also added to the final preparation. The preparation is then retained at between 0° C. and 8° C. for from 1 to 5 days before use.

All the above steps are preferably carried out under sterile conditions, and preferably the entire procedure is carried out in the venesection pack in which the donated blood is collected.

In the commercial manufacture of a stabilised whole blood preparation according to Procedure II, it is possible and may be preferable to pool a number of units of donated blood from different sources and to stabilise the resultant pool.

The stabilisation processes described herein can be applied to both normal and leukaemic cells, providing a known normal control and an abnormal (leukaemic) control.

The stabilised whole blood preparations of the invention can provide an excellent stable quality control and reference material which can be used in leucocyte immunophenotyping by both UV microscopy and flow cytometry. The preparations are of value in the quality control of the whole blood lysing procedure without any excess contamination from debris. The stabilised samples can comprise all of the normal peripheral blood leucocytes (granulocytes, monocytes and lymphocytes) or subsets thereof. The procedure can, under optimum conditions, retain the leucocyte antigenic profiles ensuring phenotyping and quality control of the procedure. The values for the common antigenic determinants can be determined and can be stable for more than 130 days. The investigator can also successfully derive values for antigens that may be of specific interest. Furthermore, the preparations can be used to quality control the differential obtained from the flow cytometer. This is a parameter that is used for the monitoring of anti-viral therapy in HIV-infected individuals.

New methods for phenotyping blood specimens are being developed which do not require the sample to be treated with a lysing agent after staining. These techniques are termed no-wash, no-lyse. The whole blood preparations of this invention can be used to provide quality control for these techniques and can also be used on flow cytometers that: analyse no-wash, no-lyse procedures.

In general the stabilised whole blood preparations of the invention can be used in quality control of UV microscopy and flow cytometric immunophenotyping techniques, both of the whole blood lysis and whole blood non-lysis techniques.

Investigations with the stabilised whole blood preparations of the invention show that they are also suitable for use in immunocytochemical analysis using techniques such as the alkaline phosphatase anti-alkaline phosphatase immunocytochemical technique (APAAP) and can for example be used to determine the antigenic profile of leucocytes on peripheral blood smears. It can be used as a day-to-day reference material or in external (interlaboratory) quality control. Multiple smears can be made in advance and then stored at −20° C. until use. The smears can be stained on a daily basis, or used as controls when staining other smears.

The stabilised whole blood preparations of the invention may also find application as standard reference materials for use in enzyme linked immunosorbent assay techniques (ELISA) and in immunoradiometric assay techniques.

Further uses of the stabilised whole blood preparations of the invention in the laboratory may include as a quality control and calibrant for haematology analysers, as a quality control material for monitoring iron deficiency by the zinc protoporphyrin technique (ZPP), and as a quality control material in the red cell folate technique. Finally, on a broader basis, the stabilised whole blood preparations of the invention may find application in the quality control of blood glucose level tests, thereby enabling diabetic patients to carry out this technique in their own homes.

The invention is illustrated by the following Example.

EXAMPLE 1

A stabilised whole blood preparation is made up as described below and its ageing characteristics compared with a similar untreated whole blood sample.

Preparation

1. Venesect 500 ml of blood into a sterile venesection pack containing 600 mg of ethylenediaminetetraacetic acid (disodium or tri potassium salt) dissolved in 50 ml of phosphate buffered saline (PBS).
2. Split anticoagulated blood into two parts (250 ml each).
3. Filter one 250 ml volume through a leucocyte filter to leucocyte deplete. Store at 4° C.
4. Centrifuge remaining 250 ml at 800 g for 1 hour.
5. Remove buffy coat (leucocyte layer).
6. To buffy coat make up volume to 250 ml with lysis solution.

Lysis Solution
  10× Stock Solution pH 7.4
  89.9 g Ammonium Chloride
  10.0 g Sodium Hydrogen Carbonate
  370 mg disodium EDTA
Above dissolved in 1000 ml of distilled $H_2O$ (1.68M $NH_4Cl$) Dilute to 2× strength with $d.H_2O$ and then add to equal volumes (1:1) of 0.2M Urea (Urea is dissolved in $d.H_2O$) to give a final lysis solution of 1× pH 7.5.
7. Lyse for 5 minutes in the dark at R.T.
8. Centrifuge for 3 minutes at 800 g and decant supernatant.
9. Wash by centrifugation at 800 g 3× with phosphate buffered saline (PBS). Decant final supernatant.
10. Resuspend the cell pellet in 20 ml of PBS.
11. Add 60 ml of filtered 0.1% of aged (>1 month) Chromium Chloride hexahydrate (pH 6.7) in PBS and incubate for 1 hour in the dark at 4° C. mixing occasionally.
12. Centrifuge for 3 minutes at 800 g and decant supernatant.
13. Resuspend in 20 ml of PBS and add 60 ml of aged (>1 month) and filtered 0.1% Chromium Chloride hexahydrate pH 6.7 in 0.35% paraformaldehyde in PBS. Incubate at 4° C. in the dark for 16–22 hours.
14. Centrifuge at 800 g for 3 minutes and decant supernatant.
15. Wash twice as in 9.
16. Resuspend the leucocytes in the leucocyte depleted whole blood detailed in 3. Add broad range antibiotics such as gentamicin, ciprofloxacin.
17. Place at 4° C. for 2–3 days until use.
  Phosphate Buffered Saline pH 7.2
  7.83 g/l Sodium Chloride
  0.36 g/l disodium EDTA
  0.28 g/l Potassium Chloride
  0.26 g/l Potassium dihydrogen phosphate (monobasic)
  2.35 g/l disodium hydrogen phosphate (dibasic)

The comparative results are illustrated in the accompanying Drawings in which:

FIG. 1 shows the flow cytometric characteristics of "fresh" blood after staining for the antigens CD3, CD4, CD8 and CD20. The staining was carried out employing the whole blood lysis technique and the positive levels related to the negative controls (a) Forward & side scatter (FSC & SSC) characteristics, (b) CD3 PE & CD20 FITC, (c) CD3 FITC & CD4 PE, (d) CD3 FITC & CD8 PE.

FIG. 2 shows the effect of ageing on the flow cytometric FSC, and SSC of "fresh" unstabilised blood over a period of 8 days (a) Day 1, (b) Day 2 (c) Day 3, (d) Day 8.

Figure 1B:
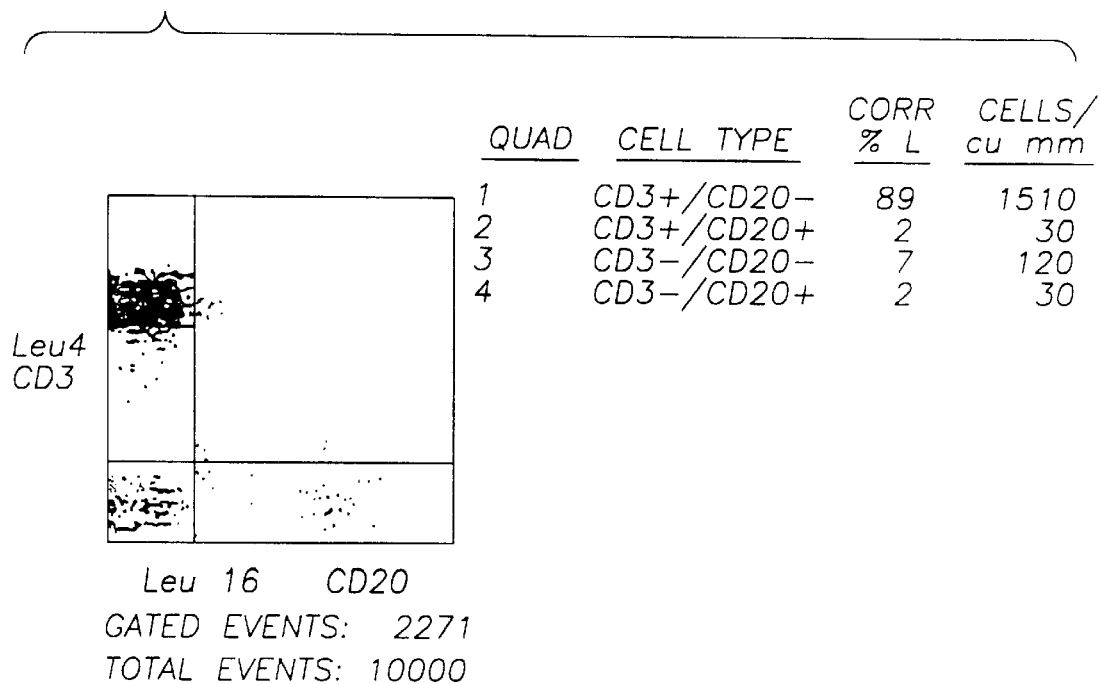
Figure 1C:
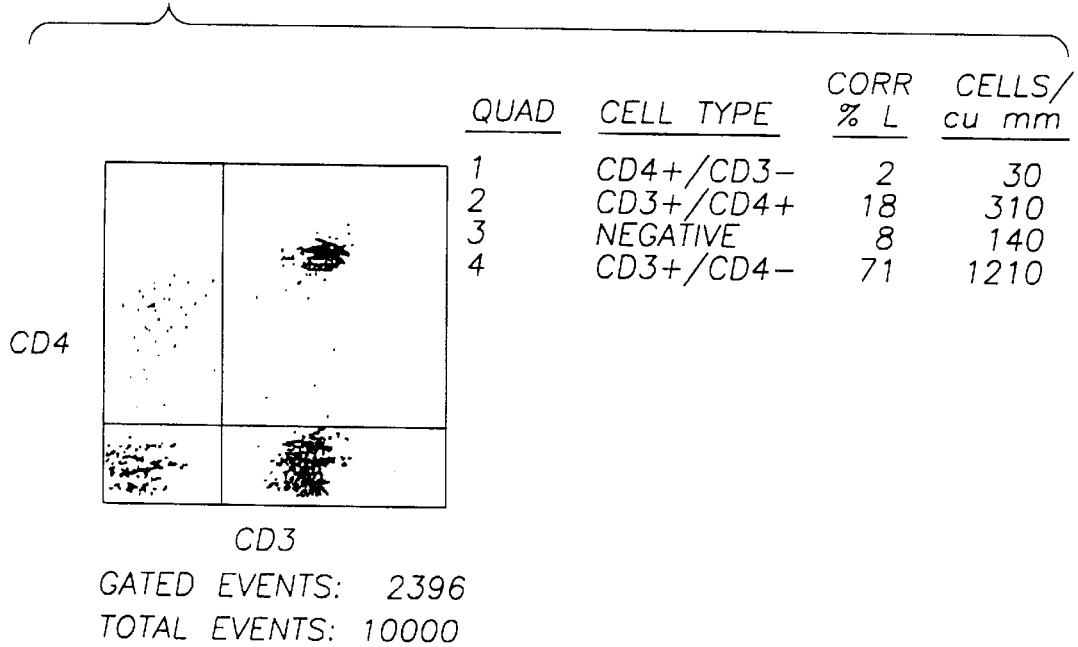
Figure 1D:
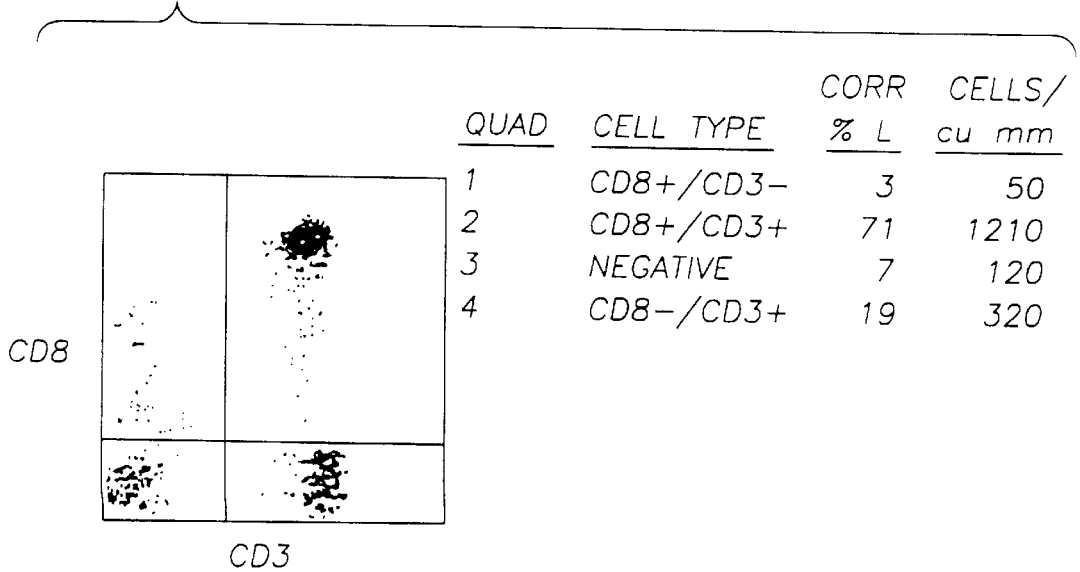
Figure 2A:
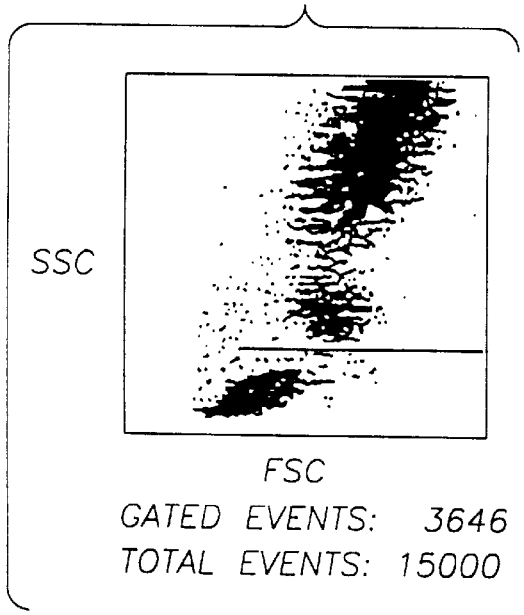
FIGS. 2a, 2b, 2c, and 2d show the effect of ageing on the flow cytometric FSC, and SSC of "fresh" unstabilised blood, over an 8 day period.
Figure 2B:
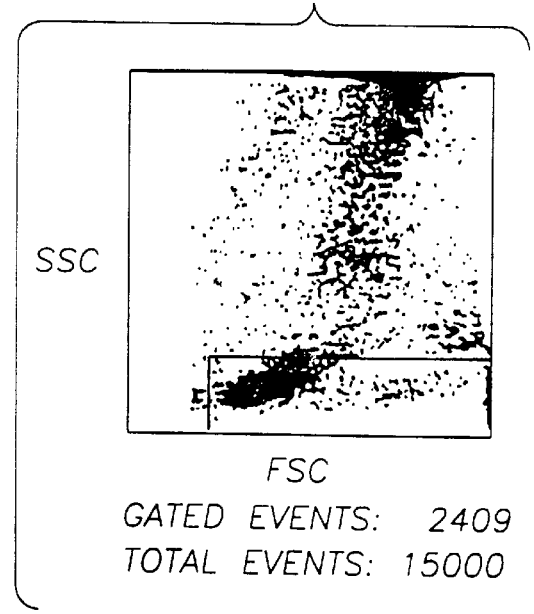
Figure 2C:
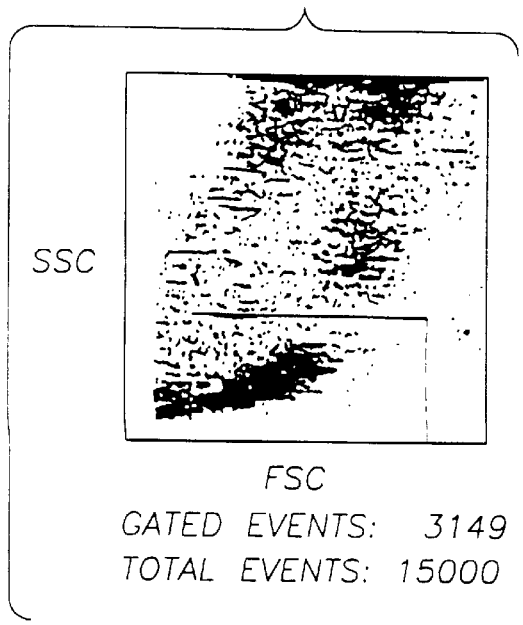
Figure 2D:
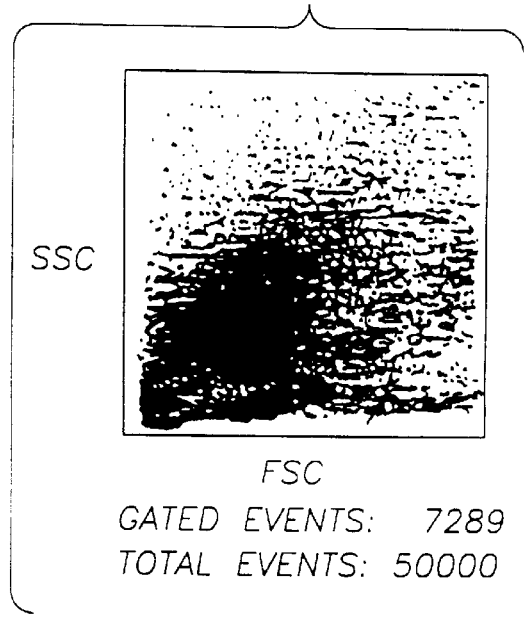
Figure 3A:
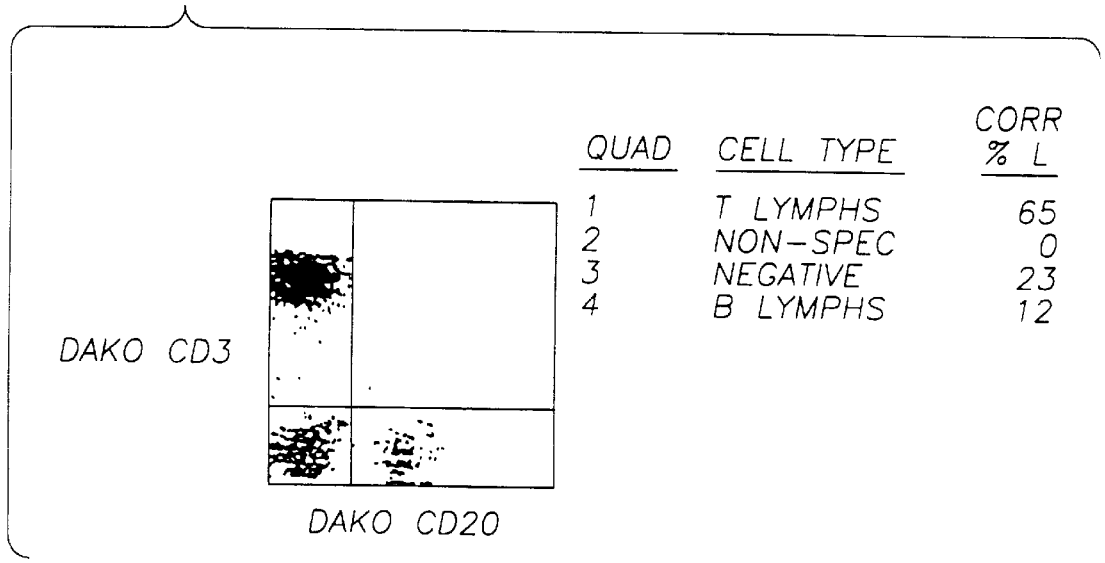
FIGS. 3a(I), 3b(I), 3a(ii), 3b(ii), 3a(iii), and 3b(iii) show the effect of ageing on the expression of antigens shown in FIGS. 1b, 1c, and 1d, over a 10 day period.
Figure 3B:
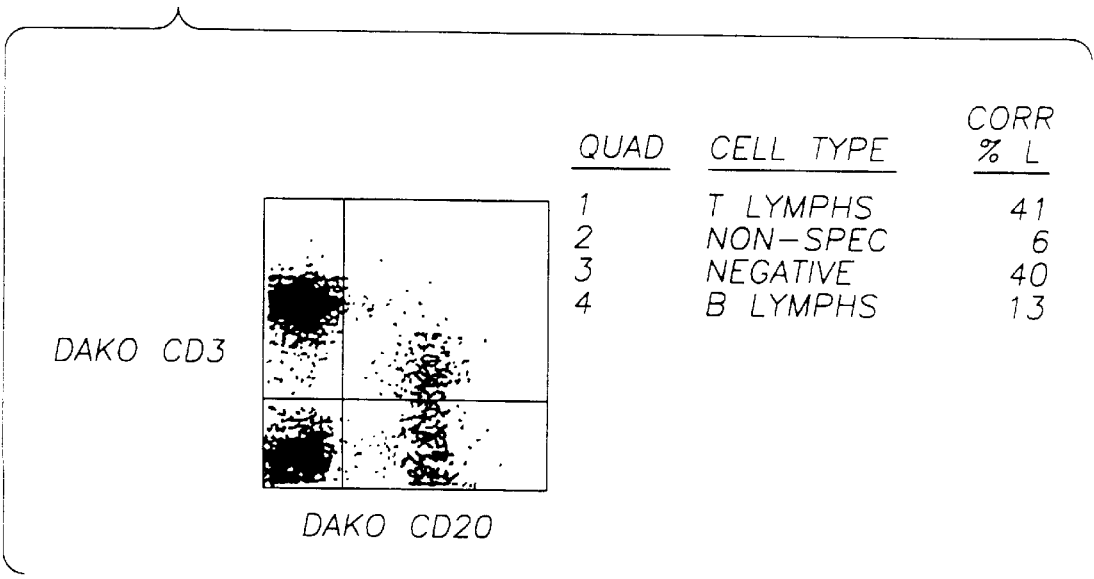

FIGS. 3*a* and 3*b* show the effect of ageing on the expression of the antigens described in FIG. 1*b, c & d* over a 10 day period 3*a* (i) (ii) (iii) Day 1, and 3*b* (i) (ii) (iii) Day 10.

FIGS. 4*a* and 4*b* show the stability of FSC, SSC and the negative control characteristics, as determined by flow cytometry, upon the stabilised whole blood preparation over a period of 57 days, 4*a* day 2, 4*b* day 57.

FIG. 5*a* and 5*b* show the stability of the antigens described in FIG. 1*b, c & d*, as measured by flow cytometry, over a 57 day period 5*a* Day 2, 5*b* Day 57.

Figure 6:
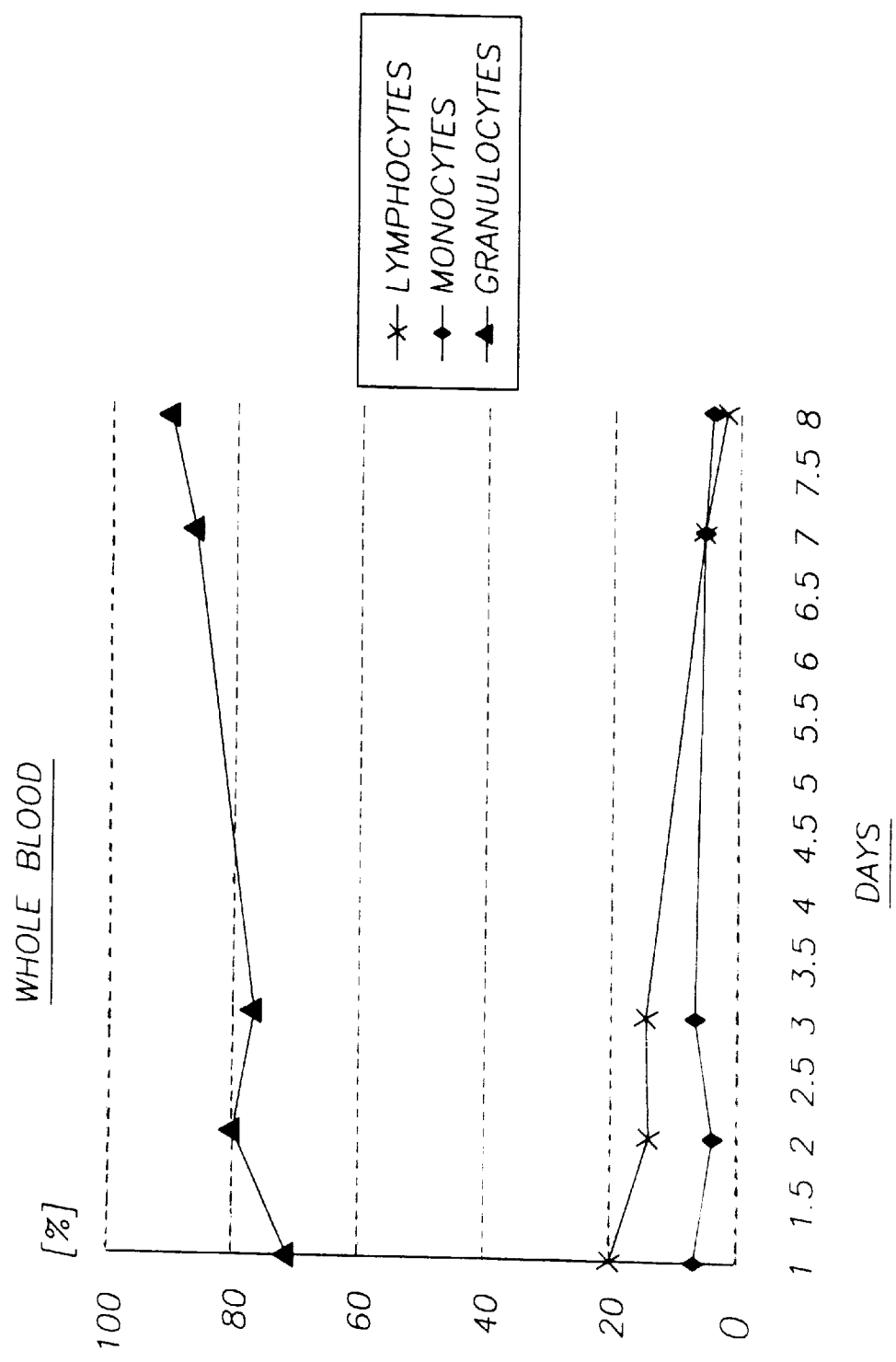
FIG. 6 shows the effect of storage on the flow cytometric leucocyte differential on "fresh" blood over an 8 day period.

FIG. 6 shows the effect of storage on the flow cytometric leucocyte differential of "fresh" blood over a period of 8 days. Further analysis after day 8 was not possible due to marked deterioration of the sample. Analysis used a FACScan flow cytometer.

FIG. 7 shows the stability of the flow cytometric differential of the stabilised blood preparation over a 22 day period. Analysis used a FACScan flow cytometer.

The flow cytometric profile in FIG. 1 shows the normal position of the lymphocytes, monocytes and granulocytes after lysis of the red cells. The antigen staining characteristics are also shown in FIG. 1*b, c, d, & e*. As the sample increases with age (FIG. 2) the flow cytometric and antigen expression characteristics alter. At day 8 the amount of debris makes the analysis unsatisfactory. The fluorescence labelling characteristics have also deteriorated as shown by FIG. 3.

FIG. 4 displays the forward and side scatter characteristics together with the negative control of the stabilised sample at day 2 and day 57. The individual populations are retained in their respective positions immediately post stabilisation. After 57 days' preservation, the forward and side scatter flow cytometric characteristics remain intact (FIG. 4*b*). In addition the antigen expression characteristics remain unaltered over this period (FIG. 5).

The stabilised blood preparation can be used to monitor the leucocyte differential. Using a specific combination of antibodies directed against the CD14 and CD45 antigens, a three-population differential can be generated. FIG. 7 shows the stability of this parameter, whereas FIG. 6 shows the instability of the "fresh" whole blood over an 8 day period. Analysis of the latter after this time was aborted due to contamination with excessive debris.

EXAMPLE 2

A stabilised whole blood preparation is made up as described below and its ageing characteristics compared with a similar untreated whole blood sample.
Preparation
1. Venesect a unit of 500 ml of blood into a sterile venesection pack containing 600 mg of ethylenediaminetetraacetic acid (disodium or tri potassium salt) dissolved in 50 ml of phosphate buffered saline solution (PBS) pH 7.2, as per Example 1.
2. Centrifuge the unit at 800 g for 1 hour. Remove and retain the plasma.
3. Wash the remaining cells twice with sterile phosphate buffered saline solution (PBS).
4. Remove the supernatant PBS.
5. Add 300 ml of filtered 0.1% aged (>1 month) Chromium Chloride hexahydrate (pH 6.7) in PBS and incubate for 1 hour in the dark at 4° C. mixing occasionally.
6. Centrifuge for 45 minutes at 800 g and decant supernatant.
7. Resuspend in 300 ml aged (>1 month) and filtered 0.1% Chromic Chloride hexahydrate pH 6.7 in 0.35% paraformaldehyde in PBS. Incubate at 4° C. in the dark for 16–22 hours.
8. Centrifuge at 800 g for 45 minutes and decant supernatant.
9. Wash twice by centrifuging at 800 g with PBS. Decant final supernatant.
10. Resuspend the stabilised whole blood in the plasma detailed in step 2. Add broad range antibiotics such as gentamicin, ciprofloxacin.
12. Place at 4° C. for 2–3 days until use.

The results are illustrated in the accompanying Drawings in which:

FIGS. 8*a* and 8*b* show the stability of FSC, SSC and the negative control characteristics, as determined by flow cytometry, upon the stabilised whole blood preparation over a period of 60 days, 4*a* day 3, 4*b* day 60.

Figure 9A:
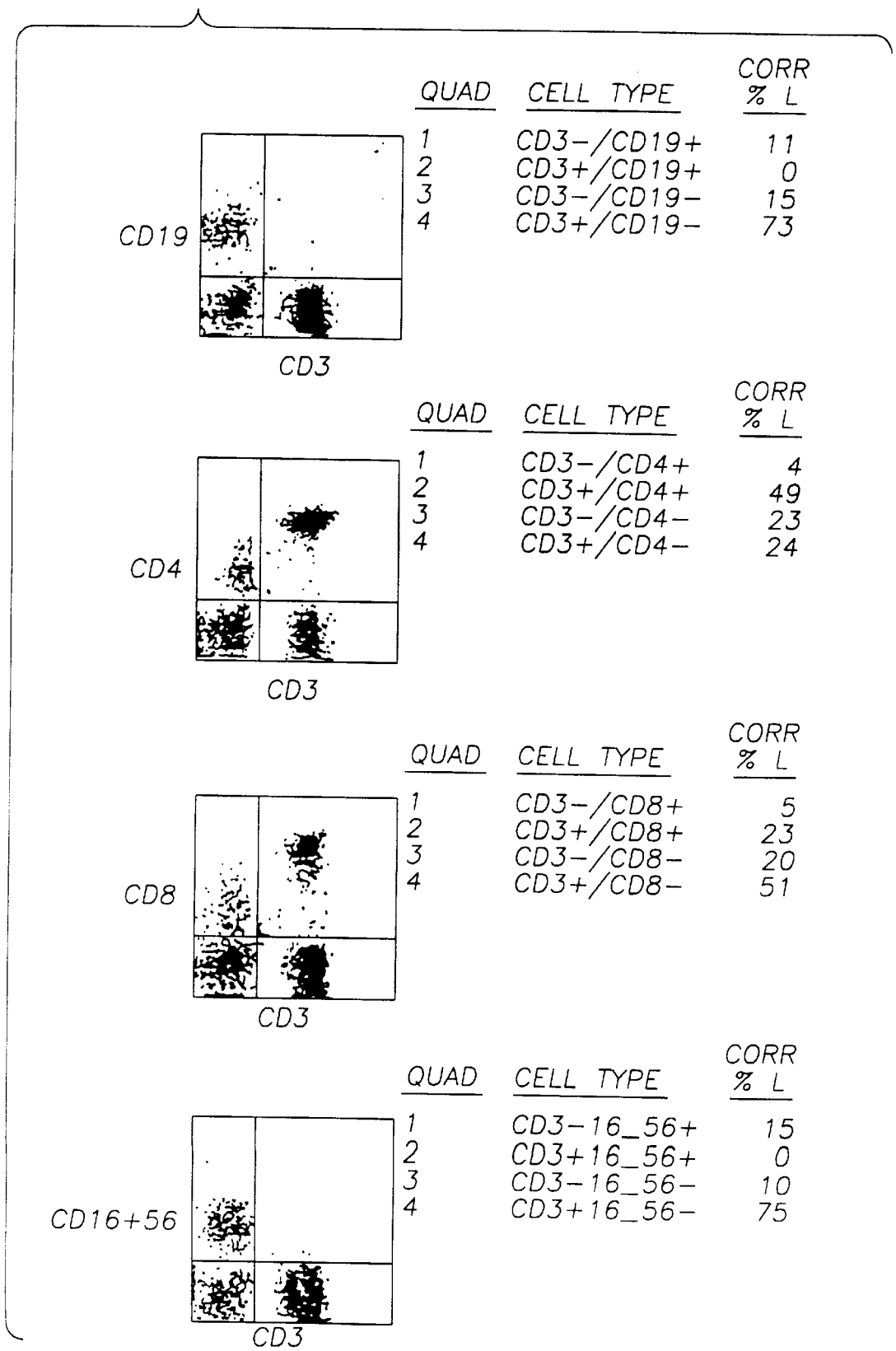
FIGS. 9a and 9b show the stability of various antigens as measured by flow cytometry, over a 57 day period.
Figure 9B:
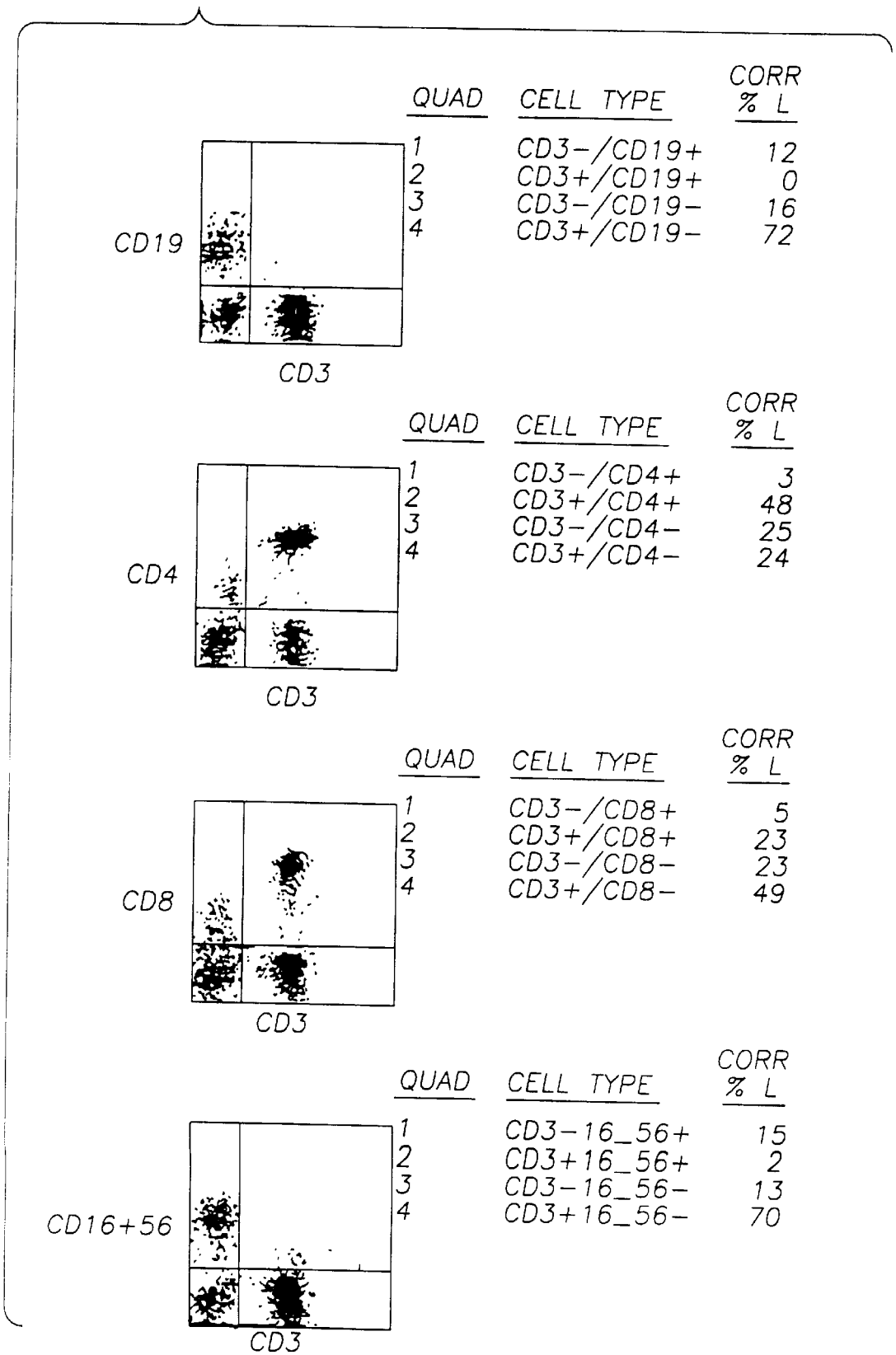

FIGS. 9*a* and 9*b* show the stability of the antigens CD3, CD4, CD8, CD19, and CD16 + CD56, as measured by flow cytometry, over a 57 day period 5*a* Day 3, 5*b* Day 60.

Figure 10:
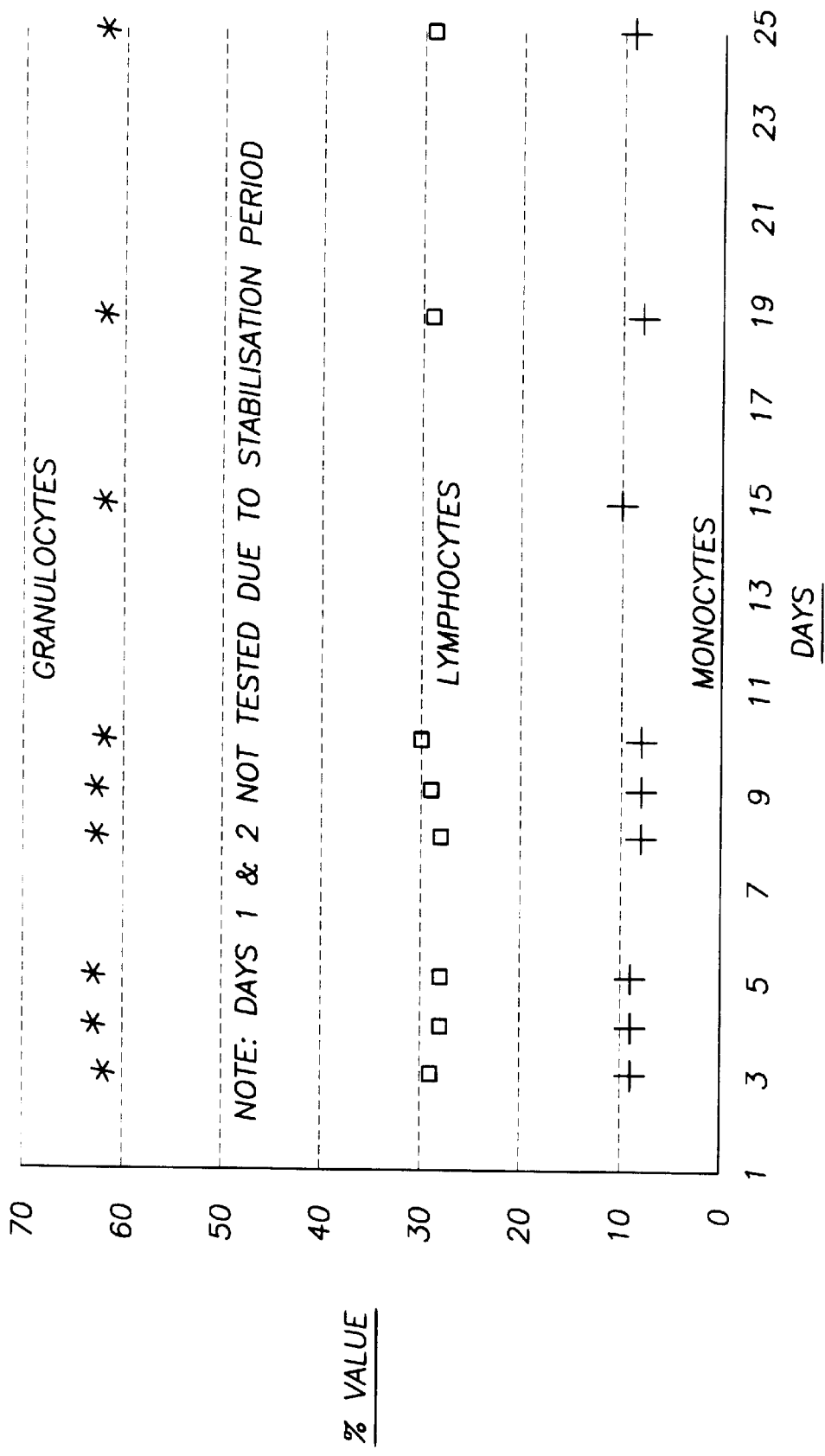
FIG. 10 shows the stability of the flow cytometric differential of the stabilised blood preparation over a 25 day period.

FIG. 10 shows the stability of the flow cytometric differential of the stabilised blood preparation over a 25 day period. Analysis used a FACScan flow cytometer.

Figure 11:
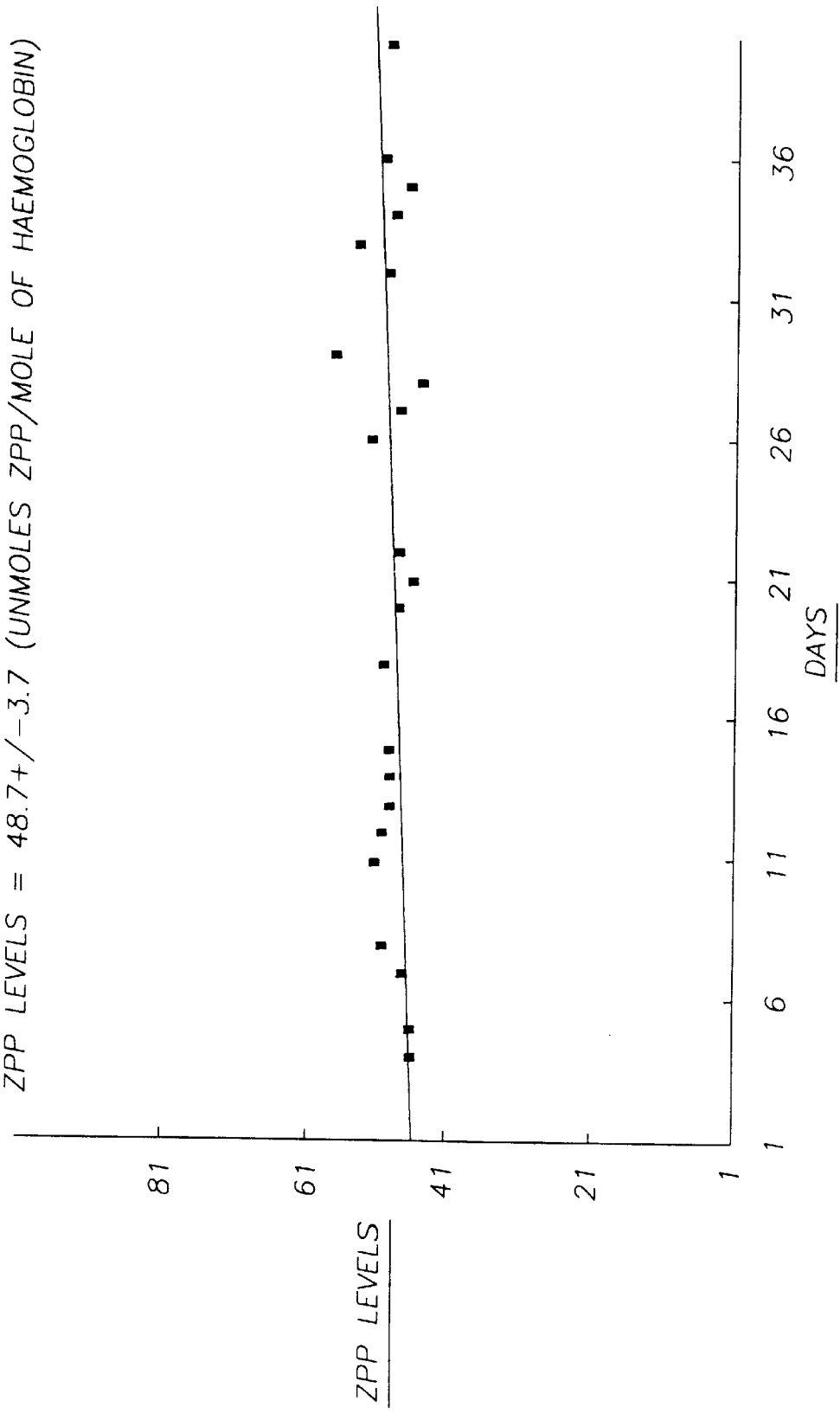
FIG. 11 shows the stability in zinc protoporphyrin (ZPP) level in a sample of the stabilised whole blood preparation over a 36 day period.

FIG. 11 shows the stability in zinc protoporphyrin (ZPP) level in a sample of the stabilised whole blood preparation over a period of 36 days measured in $\mu$moles ZPP/mole of haemoglobin.

Figure 12:
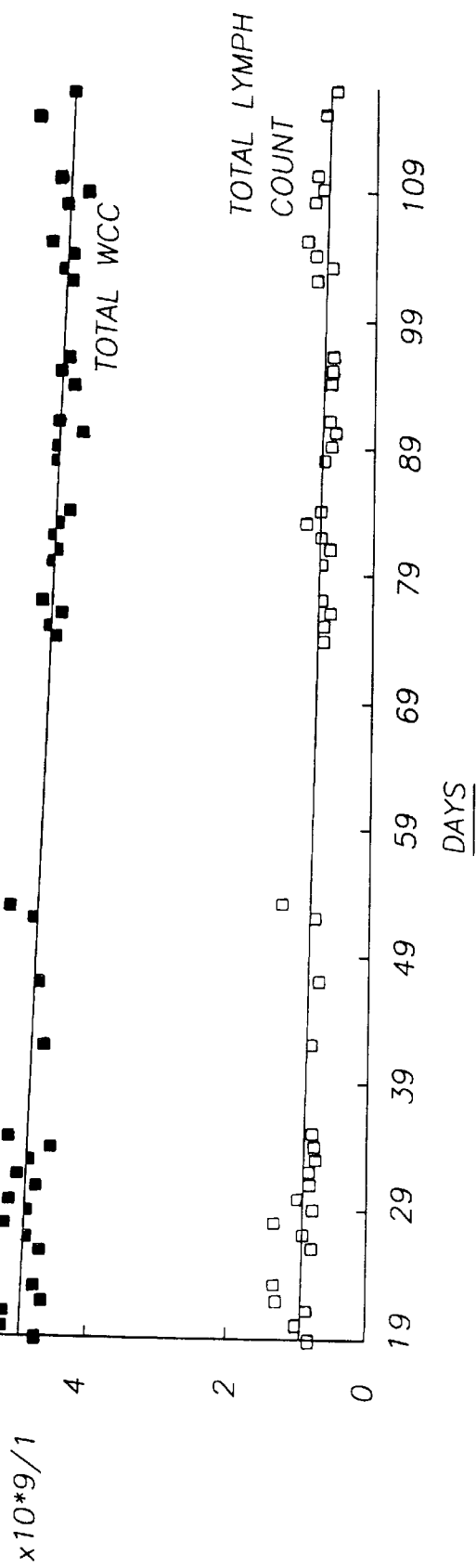
FIG. 12 shows the stability of the total white cell count and total lymphocyte count over a 117 day period for a sample of the stabilised whole blood preparations; and, FIG. 13 shows the measurement of red cell folate for samples of the stabilised whole blood preparation and fresh stored whole blood over a 50 day period.

FIG. 12 shows the stability of the total white cell count and total lymphocyte count over a 117 day period for a sample of the stabilised whole blood preparations measured using a Toa (Sysmex) NE8000 haematology analyser.

Figure 13:
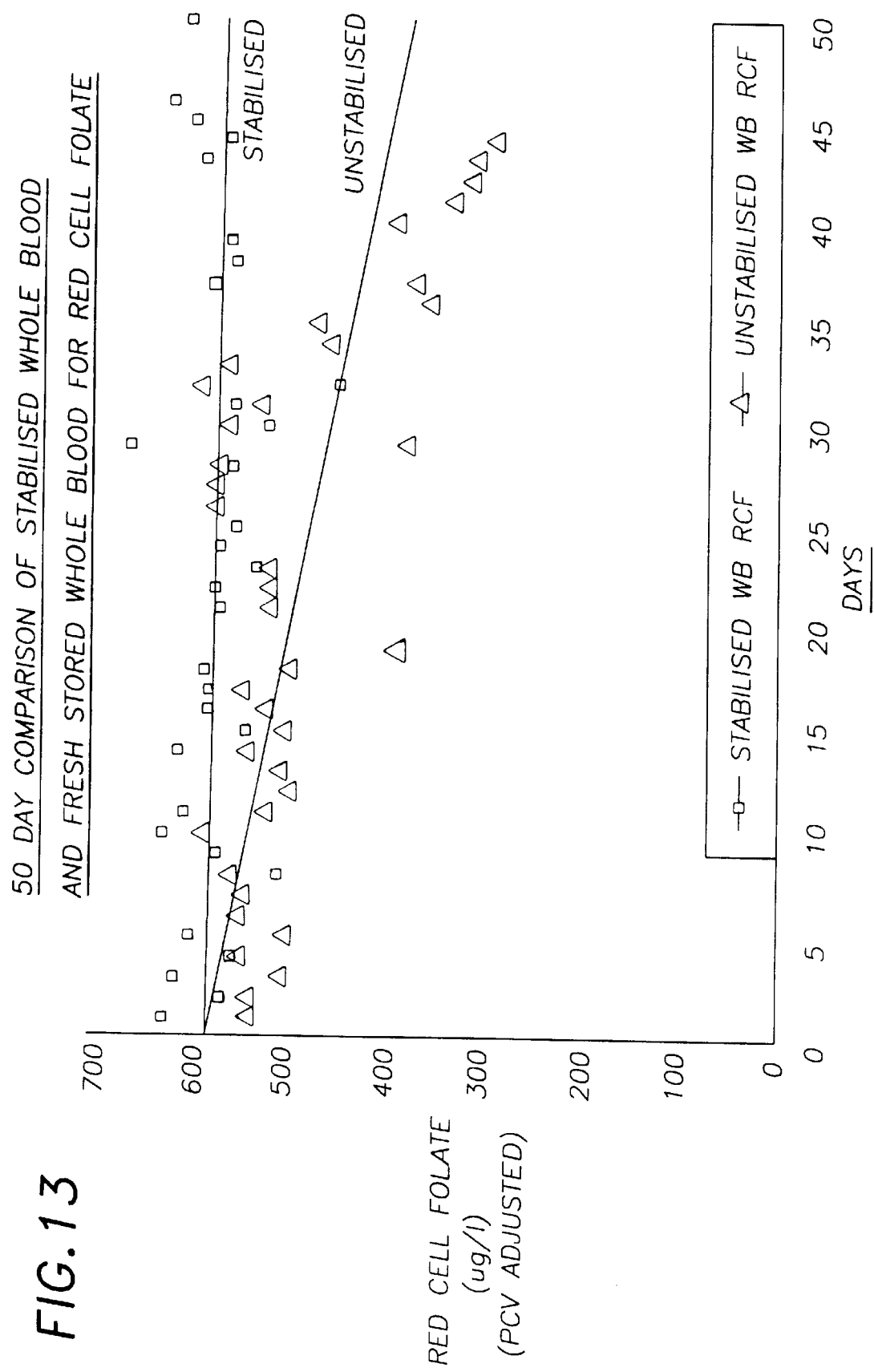

Finally, FIG. 13 shows the measurement of red cell folate for samples of the stabilised whole blood preparation and fresh stored whole blood over a 50-day period.

The flow cytometric profile in FIG. 1 shows the normal position of the lymphocytes, monocytes and granulocytes after lysis of the red cells. The antigen staining characteristics are also shown in FIG. 1b, c, d, & e. As the sample increases with age (FIG. 2) the flow cytometric and antigen expression characteristics alter. At day 8 the amount of debris makes the analysis unsatisfactory. The fluorescence labelling characteristics have also deteriorated as shown by FIG. 3.

FIGS. 8a and 8b display the forward and side scatter characteristics together with the negative control of the stabilised sample at day 3 and day 60. The individual populations are retained in their respective positions immediately post stabilisation. After 60 days' preservation the forward and side scatter flow cytometric characteristics remain intact (FIG. 4b). In addition the antigen expression characteristics remain unaltered over this period (FIGS. 9a and 9b). The same machine settings were retained throughout. These results show the marked superiority of the stabilised blood preparation of the invention over the unstabilised "control" shown in FIGS. 1 to 3.

The stabilised blood preparation can be used to monitor the leucocyte differential. Using a specific combination of antibodies directed against the CD14 and CD45 antigens, a three-population differential can be generated. FIG. 10 shows the stability of this parameter over 25 days, whereas FIG. 6 shows the instability of the "fresh" whole blood over an 8 day period. Analysis of the latter after this time was aborted due to contamination with excessive debris.

As shown in FIG. 11, ZPP levels in the stabilised whole blood preparation remain substantially constant, with only a very slight increase after 36 days. Similarly, as shown in FIG. 12, the total white cell count and total lymphocyte count are also scarcely affected by time over a 117 day period.

FIG. 13 shows the very substantial improvement obtained in the stability of red cell folate using a stabilised whole blood preparation according to the invention.

EXAMPLE 3

The procedure of Example 2 is repeated using 0.1% w/v solutions of various metal salts in 0.85% w/v phosphate buffered saline solution in Step 5. The stability of the resulting blood preparations after 8 and 12 days, as determined by FSC, SSC and negative control characteristics, is measured using a flow cytometer. The results are estimated as good, pass, or fail by visual observation of the resulting plots, and by use of Becton-Dickinson Simulset software version 2.3.

| compound | fail | pass | good |
| --- | --- | --- | --- |
| $CrCl_3$ (>1 day old) | | | X |
| $CrCl_3$ (aged 16 months) | | X | |
| $Cr_2(SO_4)_3$ | | X | |
| $CrF_3$ | | X | |
| $Cr(NO_3)_3$ | | | X |
| $Cr(acetate)_3$ | X | | |
| $MnCl_2$ | | | X |
| $PtCl_2$ | X | | |
| $ScCl_2$ | | X | |
| $VCl_3$ | | | X |
| $WCl_4$ | | X | |
| $SnCl_2$ | | | X |
| $ZnCl_2$ | X | | |
| $CeCl_3$ | X | | |
| $MgCl_2$ | X | | |
| $AlCl_3$ | X | | |
| $CuCl_2$ | X | | |
| $CuSO_4$ | | X | |
| $MoCl_3$ | | X | |
| $Pb(NO_3)_2$ | X | | |
| $FeCl_3$ | X | | |
| $TiCl_3$ | | | X |
| $K_2Cr_2O_7$ | | X | |
| Results After 12 days | | | |
| $CrCl_3$ (>1 day old) | | | X |
| $CrCl_3$ (aged 16 months) | | X | |
| $Cr_2(SO_4)_3$ | | X | |
| $CrF_3$ | X | | |
| $Cr(NO_3)_3$ | | X | |
| $Cr(acetate)_3$ | X | | |
| $MnCl_2$ | | | X |
| $PtCl_2$ | X | | |
| $SCCl_2$ | X | | |
| $VCl_3$ | X | | |
| $WCl_4$ | X | | |
| $SnCl_2$ | X | | |
| $ZnCl_2$ | X | | |
| $CeCl_3$ | X | | |
| $MgCl_2$ | X | | |
| $AlCl_3$ | X | | |
| $CuCl_2$ | X | | |
| $CuSO_4$ | X | | |
| $MoCl_3$ | X | | |
| $Pb(NO_3)_2$ | X | | |
| $FeCl_3$ | X | | |
| $TiCl_3$ | X | | |
| $K_2Cr_2O_7$ | | X | |

These results show the marked superiority of compounds of Group VIa and Group VIIa metals over other heavy metals compounds, although a number of the latter were deemed acceptable, in that improved stability over an unstabilised control, which showed a substantial deterioration after only 4 days, was obtained.

Aged chromic chloride solution (16 months) was found to be less effective than the recently prepared (>1 day old) solution, presumably due either to the formation of complex hydrated chromium ionic species in solution, or precipitation of insoluble chromium hydroxide polymeric species leaving the solution depleted of chromium ions.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract and drawings), and/or all of the steps or any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A stabilized cell composition comprising:
   leucocytes; and
   an effective amount of a stabilizing agent comprising an aged transition metal solution comprising at least one transition metal, wherein the transition metal solution is aged by allowing the metal solution to stand before use from at least 6 hours to 12 months, whereby the composition of leucocytes and transition metals is stabilized as compared to leucocytes found in fresh, unstabilized blood, wherein both the stabilized and unstabilized leucocytes are 8 days old or more, and wherein stabilization is observed by monitoring a property of blood cells that is indicative of cell stabilization.

2. The stabilized cell composition of claim 1, further comprising an aldehyde.

3. The stabilized cell composition of claim 2, wherein the aldehyde comprises paraformaldehyde.

4. The stabilized cell composition of claim 1, wherein the leucocytes are derived from blood.

5. The stabilized cell composition of claim 4, wherein the blood is whole blood.

6. A stabilized whole blood preparation comprising:
   the stabilized cell composition of claim 1; and
   leucocyte depleted whole blood.

7. The stabilized whole blood preparation of claim 6, wherein the leucocytes are washed with an aqueous solution before being added to the leucocyte depleted whole blood.

8. A stabilized cell composition produced by the process of stabilizing leucocytes comprising separating the leucocytes from whole blood or stabilizing leucocytes present in whole blood with the addition of an effective amount of a stabilizing agent comprising an aged transition metal solution, which comprises at least one transition metal, wherein the metal solution is aged by allowing the metal solution to stand before use from at least 6 hours to 12 months, and wherein the blood is pooled from different blood donation either form the same donor and/or different donors, whereby stabilization of the composition of leucocytes and transition metals is reflected in the ability of the composition to be stabilized for more than 8 days as compared to leucocytes found in fresh, unstabilized, whole blood, wherein both the stabilized and unstabilized leucocytes are 8 days old or more, and wherein stabilization is observed by monitoring a property of blood cells that is indicative of cell stabilization.

9. The stabilized cell composition of claim 8, wherein the aged transition metal solution comprises an aqueous solution of at least one transition metal comprising less than 1% weight per volume of the transition metal.

10. The stabilized cell composition of claim 9, wherein the transition metal comprises chromium.

11. The stabilized cell composition of 9, wherein the transition metal comprises manganese.

12. The stabilized cell composition of 9, wherein the transition metal comprises zinc.

13. The stabilized cell composition of claim 9, in which the aged, aqueous, transition metal solution has been aged at a pH of from 6.5 to 7.0 for at least 24 hours, wherein a visually detectable precipitate is formed, and wherein the precipitate is removed prior to use of the stabilizing agent.

14. The stabilized cell composition of claim 9, in which the transition metal solution further comprises an aldehyde comprising less than 0.1% weight per volume aldehyde.

15. The stabilized cell composition of claim 14, wherein the aldehyde comprises paraformaldehyde.

16. The stabilized cell composition of claim 8, wherein the leucocytes are pooled from different blood donations before the leucocytes are stabilized with the stabilizing agent.

17. A stabilized blood preparation comprising:
   whole blood derived from different blood donations from either the same donor and/or different donors, comprising a leucocyte component wherein the leucocytes comprise at least one property indicative of cell stabilization, and wherein the whole blood has been treated to remove a plasma component; and
   a stabilizing agent comprising an aged transition metal solution comprising at least one transition metal, wherein the transition metal solution is aged by allowing the solution to stand before use from at least 6 hours to 12 months, whereby the leucocyte component is stabilized as compared to leucocytes found in fresh, unstabilized whole blood when both the stabilized and unstabilized leucocytes are monitored for a property indicative of cell stabilization at 8 days or more.

18. The stabilized blood preparation of claim 17, further comprising a plasma component wherein the plasma component is added to the whole blood preparation after the addition of the stabilizing agent.

19. A method for preparing a stabilized blood composition comprising:
   a) removing leucocytes from blood to yield a leucocyte depleted blood component composition, wherein the blood is pooled from different blood donations either from the same donor and/or different donors;
   b) stabilizing the removed leucocytes by treatment with an effective amount of a stabilizing agent comprising an aged transition metal solution, comprising at least one transition metal, wherein the transition metal solution is aged by allowing the metal solution to stand before use from at least 6 hours to 12 months, so that the leucocytes are stabilized as compared to leucocytes found in fresh, unstabilized, whole blood when both the stabilized and unstabilized leucocytes are monitored for a property indicative of cell stabilization at 8 days or more; and
   c) adding the stabilized leucocytes comprising the stabilizing agent to the leucocyte depleted blood composition to yield a stabilized blood composition, wherein the stabilized leucocytes in the presence of the depleted blood composition also are stabilized as compared to leucocytes found in fresh, unstabilized, whole blood when both the stabilized blood composition and the unstabilized whole blood are monitored for a property indicative of cell stabilization at 8 days or more.

20. A method for preparing a stabilized blood component composition comprising:
   a) removing leucocytes from a first blood component composition, wherein the first blood component composition is pooled from different blood donations either from the same donor and/or different donors;
   b) stabilizing the removed leucocytes by treatment with an effective amount of stabilizing agent comprising an aged transition metal solution comprising at least one transition metal, wherein the transition metal solution is aged by allowing the meta solution to stand before use from at least 6 hours to 12 months, so that the leucocytes are stabilized as compared to leucocytes found in fresh, unstabilized, whole blood, when both the stabilized and unstabilized leucocytes are monitored for a property indicative of cell stabilization at 8 days or more; and c) adding the stabilized leucocytes to a second blood component composition yielding a stabilized blood component composition wherein the leucocytes in the presence of the second blood component composition remain stabilized as compared to leucocytes found in fresh, unstabilized, whole blood, when both the stabilized blood component composition and unstabilized whole blood are monitored for a property indicative of cell stabilization at 8 days or more.

21. The method of claim 20, wherein the first and/or the second blood component composition is whole blood.

22. The method of claim 20, wherein the leucocytes are stabilized with an aqueous preparation of the aged transition metal solution, wherein the solution comprises less than 1% weight per volume of metal.

23. The method of claim 22, wherein the transition metal comprises chromium.

24. The method of claim 22, wherein the transition metal comprises manganese.

25. The method of claim 22, wherein the transition metal comprises zinc.

26. The method of claim 22, wherein the aqueous solution of the transition metal has been aged at a pH of from 6.5 to 7.0 for at least 24 hours, wherein a visually detectable precipitate is formed, and wherein the precipitate is removed prior to use of the stabilizing agent.

27. The method of claim 22, further comprising an aldehyde, wherein the aldehyde comprises at least 0.1% weight per volume aldehyde.

28. The method of claim 27, wherein the aldehyde comprises paraformaldehyde.

29. A method for stabilizing a whole blood preparation comprising;

(a) acquiring the whole blood preparation comprising a leucocyte component, wherein the leucocytes comprise at least one property indicative of cell stabilization; and (b) adding an effective amount of a stabilizing agent to the whole blood preparation, wherein the stabilizing agent comprises an aged transition metal solution, wherein the metal solution is aged by allowing the metal solution to stand before use from at least 6 hours to 12 months, whereby the whole blood preparation is stabilized as compared to unstabilized, whole blood when both the stabilized and unstabilized blood preparations are monitored for a property indicative of cell stabilization at 8 days or more.

30. The method of claim 29, wherein the stabilizing agent further comprises an aldehyde.

31. The method of claim 30, wherein the aldehyde comprises paraformaldehyde.

32. The method of claim 29, wherein the transition metal comprises chromium.

33. The method of claim 29, wherein the transition metal comprises manganese.

34. The method of claim 29, wherein the transition metal comprises zinc.

35. The method of claim 29, wherein the leucocytes are stabilized with an aged, aqueous transition metal solution comprising less than 1% weight per volume of the transition metal.

36. The method of claim 35, wherein the aqueous transition metal solution has been aged at a pH of from 6.5 to 7.0 for at least 24 hours, wherein a visually detectable precipitate is formed, and wherein the precipitate is removed prior to use of the stabilizing agent.

* * * * *